US012385063B2

(12) United States Patent
Gonzalez Aseguinolaza et al.

(10) Patent No.: US 12,385,063 B2
(45) Date of Patent: Aug. 12, 2025

(54) CODON-OPTIMIZED ABCB11 TRANSGENE FOR THE TREATMENT OF PROGRESSIVE FAMILIAL INTRAHEPATIC CHOLESTASIS TYPE 2 (PFIC2)

(71) Applicant: VIVET THERAPEUTICS, Paris (FR)

(72) Inventors: Gloria Gonzalez Aseguinolaza, Barañain (ES); Cristian Smerdou, Pamplona (ES); Laura Palomo Díaz, Basauri (ES)

(73) Assignee: VIVET THERAPEUTICS, Paris (FR)

(*) Notice: Subject to any disclaimer, the term of this patent is extended or adjusted under 35 U.S.C. 154(b) by 1102 days.

(21) Appl. No.: 17/291,449

(22) PCT Filed: Nov. 6, 2019

(86) PCT No.: PCT/EP2019/080341

§ 371 (c)(1),
(2) Date: May 5, 2021

(87) PCT Pub. No.: WO2020/094693

PCT Pub. Date: May 14, 2020

(65) Prior Publication Data

US 2022/0002751 A1 Jan. 6, 2022

(30) Foreign Application Priority Data

Nov. 7, 2018 (EP) .................................... 18306458

(51) Int. Cl.

| | |
|---|---|
| ***C07H 21/02*** | (2006.01) |
| ***A61K 48/00*** | (2006.01) |
| ***C07K 14/435*** | (2006.01) |
| ***C12N 15/86*** | (2006.01) |

(52) U.S. Cl.

CPC .......... *C12N 15/86* (2013.01); *A61K 48/0058* (2013.01); *C07K 14/435* (2013.01); *C12N 2750/14123* (2013.01); *C12N 2750/14143* (2013.01); *C12N 2750/14152* (2013.01)

(58) Field of Classification Search

CPC ................................................. A61K 48/0058

See application file for complete search history.

(56) References Cited

U.S. PATENT DOCUMENTS

| | | | |
|---|---|---|---|
| 2018/0126003 A1 | 5/2018 | Hoerr | |
| 2020/0069817 A1* | 3/2020 | Liu | A61K 31/713 |

FOREIGN PATENT DOCUMENTS

| | | |
|---|---|---|
| CN | 107812003 A | 3/2018 |
| WO | 2013/151666 A2 | 10/2013 |
| WO | 2014/200816 A1 | 12/2014 |
| WO | 2016/041588 A1 | 3/2016 |
| WO | 2017/191274 A2 | 11/2017 |

OTHER PUBLICATIONS

Hayashi et al. (Hepatology, vol. 41, No. 4, 2005, pp. 916-924).*
Dijk et al. (Clinic Rev Allerg Immunol, 2015, 48, 243-253).*
Chin et al. (Bioinformatics, 30, 15, 2014, 2210-2212).*
MacDonald et al. (Molecular and Cellular Endocrinology, 190, 2002, 1-8).*
Nov. 29, 2019 International Search Report issued in International Patent Application No. PCT/EP2019/080341.
Hisamitsu Hayashi et al. "Two Common PFIC2 Mutations Are Associated With the Impaired Membrane Trafficking of BSEP/ABCB11", Hepatology, vol. 41, No. 4, Mar. 24, 2005, pp. 916-924.
Johannes Noé et al. "Functional Expression of the Canalicular Bile Salt Export Pump of Human Liver", Gastroenterology, vol. 123, No. 5, Nov. 1, 2002, pp. 1659-1666.
Lin Wang et al. "The role of bile salt export pump mutations in progressive familial intrahepatic cholestasis type II," Journal of Clinical Investigation, vol. 110, No. 7, Oct. 1, 2002, pp. 965-972.
Lisa M. Kattenhorn et al. "Adeno-Associated Virus Gene Therapy for Liver Disease", Human Gene Therapy, vol. 27, 10. 12, Dec. 1, 2016, pp. 947-961.
Ping Lam et al. "Levels of plasma membrane expression in progressive and benign mutations of the bile salt export bump (Bsep/Abcb11) correlate with severity of cholestatic diseases", American Journal of Physiology Cell Physiology, vol. 293, No. 5, 2007, pp. C1709-C1716.
Julien Baruteau et al. "Gene therapy for monogenic liver diseases: clinical successes, current challenges and future prospects", Journal of Inherited Metabolic Disease, vol. 40, No. 4, May 31, 2017, pp. 497-517.
Wendy L van der Woerd et al. "Current and future therapies for inherited cholestatic liver diseases". World Journal of Gastroenterology, vol. 23, No. 5, Jan. 7, 2017, pp. 763-775.
Jesus Prieto et al. "Gene therapy of liver diseases", Expert Opinion on Biological Therapy, vol. 4, No. 7, Jul. 1, 2004, pp. 1073-1091.
Saskia W. C. Van Mil et al. "Benign Recurrent Intrahepatic Cholestasis Type 2 is Caused by Mutations in ABCB11", Gastroenterology, vol. 127, No. 2, Aug. 1, 2004, pp. 379-384.
Nov. 29, 2019 Written Opinion issued in International Patent Application No. PCT/EP2019/080341.
Raab, David et al. "The Geneoptimizer Algorithm: Using a Sliding Window Approach to Cope With the Vast Sequence Space in Multiparameter DNA Sequence Optimization". Syst Synth Biol (2010) 4:215-225.
Mauro, Vincent P. "Codon Optimization in the Production of Recombinant Biotherapeutics: Potential Risks and Considerations". BioDrugs (2018) 32:69-81.
Feb. 14, 2023 Office Action issued in European Patent Application No. 19795591.7.

* cited by examiner

*Primary Examiner* — Amy Rose Hudson
(74) *Attorney, Agent, or Firm* — Oliff PLC

(57) ABSTRACT

A gene therapy vector is used in the treatment of progressive familial intrahepatic cholestasis type 2. More specifically, an adeno-associated virus vector includes codon-optimized sequence encoding for the BSEP for the treatment of PFIC2.

19 Claims, 10 Drawing Sheets

Specification includes a Sequence Listing.

A

B

SEQUENCE LISTING

<160> NUMBER OF SEQ ID NOS: 14

<210> SEQ ID NO 1
<211> LENGTH: 3966
<212> TYPE: DNA
<213> ORGANISM: artificial sequence
<220> FEATURE:
<223> OTHER INFORMATION: Codon-optimized sequence encoding BSEP
(co-BSEP)

<400> SEQUENCE: 1
atgagcgact ccgtgattct gagatcaatc aaaaaattcg gcgaagaaaa tgacgggttc 60
gagagcgata aatcctataa taatgacaag aagtctaggc tgcaggacga gaagaagggc 120
gatggcgtgc gggtgggctt ctttcagctg ttccggttca gcagcagcac cgacatctgg 180
ctgatgtttg tgggcagcct gtgcgccttc ctgcacggca tcgcacagcc aggcgtgctg 240
ctgatctttg gcaccatgac agacgtgttc atcgactacg atgtggagct gcaggagctg 300
cagatccctg gcaaagcctg cgtgaacaat accatcgtgt ggacaaacag ctccctgaac 360
cagaatatga ccaacggcac acgctgtggc ctgctgaata tcgagtctga gatgatcaag 420
tttgccagct actatgcagg aatcgcagtg gccgtgctga tcaccggcta catccagatt 480
tgcttctggg tcatcgcagc agcaaggcag atccagaaga tgagaaagtt ctattttcgg 540
agaatcatgc ggatggagat cggctggttt gactgtaact ctgtgggcga gctgaataca 600
agattcagcg acgacatcaa caagatcaat gacgccatcg ccgatcagat ggccctgttt 660
atccagcgga tgaccagcac aatctgtggc ttcctgctgg gcttctttag aggctggaag 720
ctgaccctgg tcatcatcag cgtgtcccca ctgatcggaa tcggagcagc aacaatcggc 780

```
ctgtctgtga gcaagttcac cgactacgag ctgaaagcct acgccaaggc aggagtggtg    840
gcagatgaag tgatcagcag catgaggacc gtggcagcct ttggcggaga gaagagggag    900
gtggagcggt acgagaagaa cctggtgttc gcccagcggt ggggcatcag aaagggcatc    960
gtgatgggct tctttacagg cttcgtgtgg tgcctgatct tcctgtgcta cgccctggcc   1020
ttttggtatg gctccaccct ggtgctggac gagggagagt ataccccctgg cacactggtg   1080
cagattttcc tgagcgtgat cgtgggcgcc ctgaacctgg gaaatgcatc cccatgcctg   1140
gaagccttcg ccacaggaag ggcagcagcc acctccatct tcgagacaat cgaccgcaag   1200
cctatcatcg actgtatgtc tgaggatggc tacaagctgg acaggatcaa gggcgagatc   1260
gagtttcaca atgtgacctt ccactatccc agccgccctg aggtgaagat cctgaacgat   1320
ctgaatatgg tcatcaagcc aggagagatg accgccctgg tgggaccctc tggagcaggc   1380
aagagcaccg ccctgcagct gatccagcgg ttttacgacc cttgcgaggg aatggtgacc   1440
gtggacggac acgacatcag gtccctgaac atccagtggc tgcgcgatca gatcggcatc   1500
gtggagcagg agccagtgct gttctctacc acaatcgccg agaatatcag atacggccgc   1560
gaggatgcca caatggagga catcgtgcag gccgccaagg aggccaacgc ctataacttc   1620
atcatggatc tgccccagca gttcgacacc ctggtgggag agggaggagg acagatgtcc   1680
ggaggccaga agcagagagt ggccatcgcc agagccctga tccgcaaccc taagatcctg   1740
ctgctggata tggccacaag cgccctggac aatgagtccg aggctatggt gcaggaggtg   1800
ctgagcaaga tccagcacgg ccacaccatc atctctgtgg cacacaggct gagcacagtg   1860
agagcagccg acaccatcat cggctttgag cacggcacag cagtggagag ggcacccac    1920
gaggagctgc tggagaggaa gggcgtgtac ttcaccctgg tgacactgca gtcccagggc   1980
aaccaggccc tgaatgagga ggacatcaag gatgccacag aggacgatat gctggcccgg   2040
accttcagca gaggctccta tcaggattct ctgagggcca gcatcaggca gcggagcaag   2100
tctcagctga gctacctggt gcacgagcca cctctggcag tggtggacca caagtccacc   2160
tatgaggagg atcgcaagga caaggacatc ccagtgcagg aggaggtgga gcctgcacca   2220
gtgaggcgca tcctgaagtt ttccgcccca gagtggccct acatgctggt gggatctgtg   2280
ggagcagcag tgaacggcac cgtgacacca ctgtatgcct tcctgttttc ccagatcctg   2340
ggcaccttct ctatccccga caaggaggag cagcggtccc agatcaatgg cgtgtgcctg   2400
ctgtttgtgg ctatgggctg cgtgagcctg tttacacagt tcctgcaggg ctacgccttc   2460
gccaagagcg gcgagctgct gaccaagcgg ctgagaaagt tcggctttag agccatgctg   2520
ggccaggaca tcgcctggtt tgacgatctg cggaacagcc caggcgccct gaccacaaga   2580
ctggccacag atgcatctca ggtgcaggga gcagcaggca gccagatcgg catgatcgtg   2640
aactccttca ccaatgtgac agtggccatg atcatcgcct tcagcttttc ctggaagctg   2700
agcctggtca tcctgtgctt cttccccttt ctggccctga gcggagcaac ccagacaagg   2760
atgctgaccg gcttcgcctc cagagacaag caggccctgg agatggtggg ccagatcaca   2820
aacgaggccc tgagcaatat caggaccgtg gcaggaatcg gcaaggagcg gcggttcatc   2880
gaggccctgg agacagagct ggagaagcct ttcaagaccg ccatccagaa ggccaacatc   2940
tacggcttct gctttgcctt cgcccagtgt atcatgttca tcgccaactc tgccagctac   3000
cgctatggcg gctacctgat cagcaatgag ggcctgcact tcagctacgt gttcagagtg   3060
atcagcgccg tggtgctgtc tgccacagcc ctgggaaggg ccttctccta caccccatct   3120
```

-continued

```
tatgccaagg ccaagatcag cgccgccagg ttctttcagc tgctggaccg ccagccaccc   3180

atcagcgtgt acaacacagc cggcgagaag tgggataatt tccagggcaa gatcgacttt   3240

gtggattgca agttcaccta tcctagcaga ccagactccc aggtgctgaa tggcctgtcc   3300

gtgtctatca gcccaggcca gacactggcc tttgtgggct cctctggctg tggcaagtcc   3360

acctctatcc agctgctgga gcggttctat gaccccgatc agggcaaagt gatgatcgac   3420

ggccacgata gcaagaaggt gaacgtgcag tttctgagat ccaatatcgg catcgtgtct   3480

caggagcctg tgctgttcgc ctgctccatc atggataaca tcaagtacgg cgacaataca   3540

aaggagatcc caatggagag agtgatcgca gcagcaaagc aggcacagct gcacgatttc   3600

gtgatgtccc tgcccgagaa gtatgagaca aacgtgggct ctcagggcag ccagctgtcc   3660

aggggcgaga agcagaggat cgcaatcgcc agggccatcg tgcgcgatcc caagatcctg   3720

ctgctggacg aggccaccag cgccctggat acagagtccg agaagaccgt gcaggtggcc   3780

ctggacaagg cccgggaggg aagaacatgt atcgtgatcg cccacagact gagcaccatc   3840

cagaatgccg acatcatcgc cgtgatggcc cagggcgtgg tcatcgagaa gggcacccac   3900

gaggaactga tggcacagaa aggggcttac tacaaactgg tcacaacagg ctcacctatc   3960

tcatag                                                              3966
```

<210> SEQ ID NO 2
<211> LENGTH: 3966
<212> TYPE: DNA
<213> ORGANISM: artificial sequence
<220> FEATURE:
<223> OTHER INFORMATION: Codon-optimized sequence encoding BSEP #2
(co-BSEP-2)

<400> SEQUENCE: 2

```
atgtctgatt ctgtgatcct gagatccatc aagaaatttg gggaagagaa tgatggcttt     60

gagtctgaca agagctacaa caatgacaag aaaagcaggc tgcaggatga gaaaaagggt    120

gatggtgtca gagtgggctt cttccagctg ttcagattca gcagcagcac agacatctgg    180

ctgatgtttg tgggcagcct gtgtgccttc ctgcatggaa ttgctcagcc tggggtgctg    240

ctgatctttg gcaccatgac agatgtgttc attgactatg atgtggaact gcaagagctg    300

cagatccctg gcaaggcttg tgtgaacaac accattgtgt ggaccaacag cagcctgaac    360

cagaacatga ccaatggcac cagatgtggc ctgctgaaca tagagtctga gatgatcaag    420

tttgccagct actatgctgg cattgctgtg gcagtgctga tcacaggcta catccagatc    480

tgcttttggg tcatagctgc tgccagacag atccagaaga tgaggaagtt ctactttaga    540

aggatcatga ggatggaaat tggatggttt gactgcaact ctgtgggaga gctgaacacc    600

agattctctg atgacatcaa caagatcaat gatgccattg ctgaccagat ggccctgttc    660

atccagagga tgaccagcac catctgtggc tttctgctgg gctttttcag aggctggaag    720

ctgaccctgg ttatcatctc tgtgtcccca ctgattggca ttggagctgc caccattggc    780

ctgtctgtgt ccaagttcac agactatgag ctgaaagcct atgccaaggc tggtgttgtg    840

gctgatgaag tgatcagctc catgagaaca gtggctgcct ttggtggtga aaagagggaa    900

gttgagagat atgagaagaa cctggtgttt gcccagagat ggggcatcag aaagggcatt    960

gtgatgggat tcttcacagg ctttgtgtgg tgcctgatct tcctgtgcta tgccctggcc   1020

ttttggtatg gcagcaccct ggttcttgat gaaggggagt acacccctgg aactctggtg   1080

cagatctttc tgtctgtgat tgtgggagcc ctgaacctgg gcaatgcctc tccatgtctg   1140
```

-continued gaagcctttg ccacaggcag agctgctgct accagcatct ttgagacaat tgacagaaag 1200
cccatcattg actgcatgtc tgaggatggc tacaagctgg acaggatcaa aggggagatt 1260
gagttccaca acgtgacctt tcactacccc agcagacctg aagtgaagat cctgaatgac 1320
ctgaacatgg tcatcaagcc tggggagatg acagcccttg tgggacctag tggtgctggc 1380
aaatctacag ccctgcagct gatccagaga ttctatgacc cctgtgaagg catggtcaca 1440
gtggatggcc atgacatcag atctctgaac atccagtggc tgagggacca gattggaatt 1500
gtggaacaag agcctgtgct gttcagcacc accattgcag agaacatcag atatggcagg 1560
gaagatgcca caatggaaga tattgtgcag gctgccaaag aggccaacgc ctacaacttc 1620
atcatggacc tgcctcagca gtttgacacc cttgttggag agggtggtgg ccaaatgagt 1680
ggtggacaga aacagagagt ggccattgct agagccctga tcagaaaccc caagatcctg 1740
ctgctggaca tggctacatc tgccctggac aatgagtctg aggctatggt gcaagaggtg 1800
ctgagcaaga tccagcatgg ccacaccatc attagtgtgg cccacagact gagcacagtc 1860
agggctgctg acacaatcat tggatttgag catggcacag cagtggaaag gggcacccat 1920
gaggaactgc tggaaagaaa aggggtctac ttcaccctgg tcaccctgca gtctcagggc 1980
aatcaggccc tgaatgaaga ggacatcaag gatgccactg aggatgacat gctggccaga 2040
accttcagca gaggcagcta ccaggatagc ctgagagcca gcatcagaca gagaagcaag 2100
agccagctga gctacctggt gcatgaacct ccactggctg tggtggacca caagtccacc 2160
tatgaggaag ataggaagga caaggacatc cctgtgcaag aagaggtgga acctgctcct 2220
gtcagaagaa tcctgaagtt ttctgcccct gagtggccct acatgcttgt gggttctgtt 2280
ggggctgctg tgaatggcac agtgacccct ctgtatgcct ttctgttctc ccagatcctg 2340
ggcaccttta gcatccctga caaagaggaa cagaggtccc agatcaatgg tgtctgcctg 2400
ctctttgtgg ctatgggctg tgtgtccctg tttacccagt tcctgcaggg atatgccttt 2460
gctaagagtg gggagctgct cacaaagagg ctgagaaagt ttggcttcag agccatgctt 2520
ggccaggaca ttgcttggtt tgatgacctg agaaacagcc ctggggctct gaccacaaga 2580
ctggctacag atgctagcca ggtgcagggt gcagcaggca gccaaattgg catgattgtg 2640
aacagcttca ccaatgtgac agtggccatg atcattgcct tcagcttcag ctggaaactg 2700
agccttgtga tcctctgctt cttccccttt ctggccctgt ctggggctac ccagacaaga 2760
atgctgactg gctttgcctc cagagacaag caggccctgg aaatggttgg acagatcacc 2820
aatgaggccc tgtccaacat caggacagtg gcaggcattg gcaaagagag aagattcatt 2880
gaggcccttg agacagagct tgagaagccc ttcaagacag ccatccagaa agctaacatc 2940
tatgggttct gctttgcttt tgcccagtgc atcatgttca ttgccaactc agccagctac 3000
agatatggtg gctacctgat ctctaatgag ggcctgcact tcagctatgt gttcagagtg 3060
atctctgctg tggtgctgtc tgccactgct ctgggcagag cctttagcta cacccctagc 3120
tatgccaaag ccaagatctc tgcagccaga ttctttcagc tgctggatag acagcctcct 3180
atcagtgtgt acaacacagc tggggagaag tgggacaact tccagggcaa gattgacttt 3240
gtggattgca agttcaccta tcctagcaga ccagactctc aggtgctgaa tggactgagt 3300
gtgtctatca gccctggcca gacactggcc tttgtgggaa gctctggatg tggcaagagc 3360
accagcatcc agctgcttga gaggttctat gatccagacc agggcaaagt gatgattgat 3420
gggcatgaca gcaagaaagt gaatgtgcag ttcctgaggt ccaacattgg gattgtgtcc 3480
caagaacctg ttctgtttgc ctgcagcatc atggataaca ttaagtatgg ggacaacacc 3540

```
aaagaaatcc ctatggaaag agtgattgct gcagccaagc aggcacagct gcatgatttt   3600

gtgatgagcc tgcctgagaa gtatgagaca aatgtgggct cccagggcag ccagctgtct   3660

agaggggaaa aacagagaat tgccatagcc agggccatag tcagagatcc taagattctg   3720

ctcctggatg aggccacctc tgctctggat acagagtctg aaaagacagt ccaggtggca   3780

ctggacaagg ccagagaggg cagaacctgt attgtgattg cccataggct gtccacaatc   3840

caaaatgctg acatcattgc agtgatggcc caaggggttg tgattgagaa gggaacacat   3900

gaagaactca tggcccaaaa aggggcctat tataagctgg tcaccactgg cagccccatc   3960

agctag                                                              3966
```

<210> SEQ ID NO 3
<211> LENGTH: 4734
<212> TYPE: DNA
<213> ORGANISM: artificial sequence
<220> FEATURE:
<223> OTHER INFORMATION: recombinant AAV vector comprising codon-optimized sequence encoding BSEP

<400> SEQUENCE: 3

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgcg aattccatgg taccaggcat caagacacgt    180

gcgccacccc ctccaccttg gacacaggac gctgtggttt ctgagccagg tacaatgact    240

cctttcggta agtgcagtgg aagctgtaca ctgcccaggc aaagcgtccg ggcagcgtag    300

gcgggcgact cagatcccag ccagtggact tagcccctgt ttgctcctcc gataactggg    360

gtgaccttgg ttaatattca ccagcagcct cccccgttgc cctctggat ccactgctta     420

aatacggacg aggacagggc cctgtctcct cagcttcagg caccaccact gacctgggac    480

agtgaaggcc tgtcgacgga tccgagctcg ccgccaccat gagcgactcc gtgattctga    540

gatcaatcaa aaaattcggc gaagaaaatg acgggttcga gagcgataaa tcctataata    600

atgacaagaa gtctaggctg caggacgaga agaagggcga tggcgtgcgg gtgggcttct    660

ttcagctgtt ccggttcagc agcagcaccg acatctggct gatgtttgtg ggcagcctgt    720

gcgccttcct gcacggcatc gcacagccag gcgtgctgct gatctttggc accatgacag    780

acgtgttcat cgactacgat gtggagctgc aggagctgca gatccctggc aaagcctgcg    840

tgaacaatac catcgtgtgg acaaacagct ccctgaacca gaatatgacc aacggcacac    900

gctgtggcct gctgaatatc gagtctgaga tgatcaagtt tgccagctac tatgcaggaa    960

tcgcagtggc cgtgctgatc accggctaca tccagatttg cttctgggtc atcgcagcag   1020

caaggcagat ccagaagatg agaaagttct attttcggag aatcatgcgg atggagatcg   1080

gctggtttga ctgtaactct gtgggcgagc tgaatacaag attcagcgac gacatcaaca   1140

agatcaatga cgccatcgcc gatcagatgg ccctgtttat ccagcggatg accagcacaa   1200

tctgtggctt cctgctgggc ttctttagag gctggaagct gaccctggtc atcatcagcg   1260

tgtccccact gatcggaatc ggagcagcaa caatcggcct gtctgtgagc aagttcaccg   1320

actacgagct gaaagcctac gccaaggcag gagtggtggc agatgaagtg atcagcagca   1380

tgaggaccgt ggcagccttt ggcggagaga agagggaggt ggagcggtac gagaagaacc   1440

tggtgttcgc ccagcggtgg ggcatcagaa agggcatcgt gatgggcttc tttacaggct   1500

tcgtgtggtg cctgatcttc ctgtgctacg ccctggcctt ttggtatggc tccaccctgg   1560
```

-continued

```
tgctggacga gggagagtat acccctggca cactggtgca gattttcctg agcgtgatcg   1620
tgggcgccct gaacctggga aatgcatccc catgcctgga agccttcgcc acaggaaggg   1680
cagcagccac ctccatcttc gagacaatcg accgcaagcc tatcatcgac tgtatgtctg   1740
aggatggcta caagctggac aggatcaagg gcgagatcga gtttcacaat gtgaccttcc   1800
actatcccag ccgccctgag gtgaagatcc tgaacgatct gaatatggtc atcaagccag   1860
gagagatgac cgccctggtg ggaccctctg gagcaggcaa gagcaccgcc ctgcagctga   1920
tccagcggtt ttacgaccct tgcgagggaa tggtgaccgt ggacggacac gacatcaggt   1980
ccctgaacat ccagtggctg cgcgatcaga tcggcatcgt ggagcaggag ccagtgctgt   2040
tctctaccac aatcgccgag aatatcagat acggccgcga ggatgccaca atggaggaca   2100
tcgtgcaggc cgccaaggag gccaacgcct ataacttcat catggatctg ccccagcagt   2160
tcgacaccct ggtgggagag ggaggaggac agatgtccgg aggccagaag cagagagtgg   2220
ccatcgccag agccctgatc cgcaacccta agatcctgct gctggatatg gccacaagcg   2280
ccctggacaa tgagtccgag gctatggtgc aggaggtgct gagcaagatc cagcacggcc   2340
acaccatcat ctctgtggca cacaggctga gcacagtgag agcagccgac accatcatcg   2400
gctttgagca cggcacagca gtggagaggg gcacccacga ggagctgctg gagaggaagg   2460
gcgtgtactt caccctggtg acactgcagt cccagggcaa ccaggccctg aatgaggagg   2520
acatcaagga tgccacagag gacgatatgc tggcccggac cttcagcaga ggctcctatc   2580
aggattctct gagggccagc atcaggcagc ggagcaagtc tcagctgagc tacctggtgc   2640
acgagccacc tctggcagtg gtggaccaca agtccaccta tgaggaggat cgcaaggaca   2700
aggacatccc agtgcaggag gaggtggagc ctgcaccagt gaggcgcatc ctgaagtttt   2760
ccgccccaga gtggccctac atgctggtgg gatctgtggg agcagcagtg aacggcaccg   2820
tgacaccact gtatgccttc ctgttttccc agatcctggg caccttctct atccccgaca   2880
aggaggagca gcggtcccag atcaatggcg tgtgcctgct gtttgtggct atgggctgcg   2940
tgagcctgtt tacacagttc ctgcagggct acgccttcgc caagagcggc gagctgctga   3000
ccaagcggct gagaaagttc ggctttagag ccatgctggg ccaggacatc gcctggtttg   3060
acgatctgcg gaacagccca ggcgccctga ccacaagact ggccacagat gcatctcagg   3120
tgcagggagc agcaggcagc cagatcggca tgatcgtgaa ctccttcacc aatgtgacag   3180
tggccatgat catcgccttc agcttttcct ggaagctgag cctggtcatc ctgtgcttct   3240
tccccttctt ggccctgagc ggagcaaccc agacaaggat gctgaccggc ttcgcctcca   3300
gagacaagca ggccctggag atggtgggcc agatcacaaa cgaggccctg agcaatatca   3360
ggaccgtggc aggaatcggc aaggagcggc ggttcatcga ggccctggag acagagctgg   3420
agaagccttt caagaccgcc atccagaagg ccaacatcta cggcttctgc tttgccttcg   3480
cccagtgtat catgttcatc gccaactctg ccagctaccg ctatggcggc tacctgatca   3540
gcaatgaggg cctgcacttc agctacgtgt tcagagtgat cagcgccgtg gtgctgtctg   3600
ccacagccct gggaagggcc ttctcctaca ccccatctta tgccaaggcc aagatcagcg   3660
ccgccaggtt ctttcagctg ctggaccgcc agccacccat cagcgtgtac aacacagccg   3720
gcgagaagtg ggataatttc cagggcaaga tcgactttgt ggattgcaag ttcacctatc   3780
ctagcagacc agactcccag gtgctgaatg gcctgtccgt gtctatcagc ccaggccaga   3840
cactggcctt tgtgggctcc tctggctgtg gcaagtccac ctctatccag ctgctggagc   3900
```

-continued

```
ggttctatga ccccgatcag ggcaaagtga tgatcgacgg ccacgatagc aagaaggtga   3960

acgtgcagtt tctgagatcc aatatcggca tcgtgtctca ggagcctgtg ctgttcgcct   4020

gctccatcat ggataacatc aagtacggcg acaatacaaa ggagatccca atggagagag   4080

tgatcgcagc agcaaagcag gcacagctgc acgatttcgt gatgtccctg cccgagaagt   4140

atgagacaaa cgtgggctct cagggcagcc agctgtccag ggcgagaag cagaggatcg   4200

caatcgccag ggccatcgtg cgcgatccca agatcctgct gctggacgag gccaccagcg   4260

ccctggatac agagtccgag aagaccgtgc aggtggccct ggacaaggcc cgggagggaa   4320

gaacatgtat cgtgatcgcc cacagactga gcaccatcca gaatgccgac atcatcgccg   4380

tgatggccca gggcgtggtc atcgagaagg gcacccacga ggaactgatg gcacagaaag   4440

gggcttacta caaactggtc acaacaggct cacctatctc atagggatcc atatgatatc   4500

aataaagacc tcttattttc attcatcagg tgtggttggt ttttttgtgt gggggctcga   4560

gatctgagga acccctagtg atggaggcgg ccgcaggaac ccctagtgat ggagttggcc   4620

actccctctc tgcgcgctcg ctcgctcact gaggccgggc gaccaaaggt cgcccgacgc   4680

ccgggctttg cccgggcggc ctcagtgagc gagcgagcgc gcagctgcct gcag         4734
```

<210> SEQ ID NO 4
<211> LENGTH: 4734
<212> TYPE: DNA
<213> ORGANISM: artificial sequence
<220> FEATURE:
<223> OTHER INFORMATION: recombinant AAV vector comprising codon-
optimized sequence encoding BSEP #2

<400> SEQUENCE: 4

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgcg aattccatgg taccaggcat caagacacgt    180

gcgccacccc ctccaccttg gacacaggac gctgtggttt ctgagccagg tacaatgact    240

cctttcggta agtgcagtgg aagctgtaca ctgcccaggc aaagcgtccg ggcagcgtag    300

gcgggcgact cagatcccag ccagtggact tagcccctgt ttgctcctcc gataactggg    360

gtgaccttgg ttaatattca ccagcagcct cccccgttgc cctctggat ccactgctta    420

aatacggacg aggacagggc cctgtctcct cagcttcagg caccaccact gacctgggac    480

agtgaaggcc tgtcgacgga tccgagctcg ccgccaccat gtctgattct gtgatcctga    540

gatccatcaa gaaatttggg gaagagaatg atggctttga gtctgacaag agctacaaca    600

atgacaagaa aagcaggctg caggatgaga aaaagggtga tggtgtcaga gtgggcttct    660

tccagctgtt cagattcagc agcagcacag acatctggct gatgtttgtg ggcagcctgt    720

gtgccttcct gcatggaatt gctcagcctg ggtgctgct gatctttggc accatgacag    780

atgtgttcat tgactatgat gtggaactgc aagagctgca gatccctggc aaggcttgtg    840

tgaacaacac cattgtgtgg accaacagca gcctgaacca gaacatgacc aatggcacca    900

gatgtggcct gctgaacata gagtctgaga tgatcaagtt tgccagctac tatgctggca    960

ttgctgtggc agtgctgatc acaggctaca tccagatctg cttttgggtc atagctgctg   1020

ccagacagat ccagaagatg aggaagttct actttagaag gatcatgagg atggaaattg   1080

gatggtttga ctgcaactct gtgggagagc tgaacaccag attctctgat gacatcaaca   1140

agatcaatga tgccattgct gaccagatgg ccctgttcat ccagaggatg accagcacca   1200
```

-continued

```
tctgtggctt tctgctgggc tttttcagag gctggaagct gaccctggtt atcatctctg   1260
tgtccccact gattggcatt ggagctgcca ccattggcct gtctgtgtcc aagttcacag   1320
actatgagct gaaagcctat gccaaggctg gtgttgtggc tgatgaagtg atcagctcca   1380
tgagaacagt ggctgccttt ggtggtgaaa agagggaagt tgagagatat gagaagaacc   1440
tggtgtttgc ccagagatgg ggcatcagaa agggcattgt gatgggattc ttcacaggct   1500
ttgtgtggtg cctgatcttc ctgtgctatg ccctggcctt ttggtatggc agcaccctgg   1560
ttcttgatga aggggagtac acccctggaa ctctggtgca gatctttctg tctgtgattg   1620
tgggagccct gaacctgggc aatgcctctc catgtctgga agcctttgcc acaggcagag   1680
ctgctgctac cagcatcttt gagacaattg acagaaagcc catcattgac tgcatgtctg   1740
aggatggcta caagctggac aggatcaaag gggagattga gttccacaac gtgacctttc   1800
actaccccag cagacctgaa gtgaagatcc tgaatgacct gaacatggtc atcaagcctg   1860
gggagatgac agcccttgtg ggacctagtg gtgctggcaa atctacagcc ctgcagctga   1920
tccagagatt ctatgacccc tgtgaaggca tggtcacagt ggatggccat gacatcagat   1980
ctctgaacat ccagtggctg agggaccaga ttggaattgt ggaacaagag cctgtgctgt   2040
tcagcaccac cattgcagag aacatcagat atggcaggga agatgccaca atggaagata   2100
ttgtgcaggc tgccaaagag gccaacgcct acaacttcat catggacctg cctcagcagt   2160
ttgacaccct tgttggagag ggtggtggcc aaatgagtgg tggacagaaa cagagagtgg   2220
ccattgctag agccctgatc agaaacccca agatcctgct gctggacatg gctacatctg   2280
ccctggacaa tgagtctgag gctatggtgc aagaggtgct gagcaagatc cagcatggcc   2340
acaccatcat tagtgtggcc cacagactga gcacagtcag ggctgctgac acaatcattg   2400
gatttgagca tggcacagca gtggaaaggg gcacccatga ggaactgctg gaaagaaaag   2460
gggtctactt caccctggtc accctgcagt ctcagggcaa tcaggccctg aatgaagagg   2520
acatcaagga tgccactgag gatgacatgc tggccagaac cttcagcaga ggcagctacc   2580
aggatagcct gagagccagc atcagacaga gaagcaagag ccagctgagc tacctggtgc   2640
atgaacctcc actggctgtg gtggaccaca agtccaccta tgaggaagat aggaaggaca   2700
aggacatccc tgtgcaagaa gaggtggaac ctgctcctgt cagaagaatc ctgaagtttt   2760
ctgcccctga gtggccctac atgcttgtgg gttctgttgg ggctgctgtg aatggcacag   2820
tgacccctct gtatgccttt ctgttctccc agatcctggg cacctttagc atccctgaca   2880
aagaggaaca gaggtcccag atcaatggtg tctgcctgct ctttgtggct atgggctgtg   2940
tgtccctgtt tacccagttc ctgcagggat atgcctttgc taagagtggg gagctgctca   3000
caaagaggct gagaaagttt ggcttcagag ccatgcttgg ccaggacatt gcttggtttg   3060
atgacctgag aaacagccct ggggctctga ccacaagact ggctacagat gctagccagg   3120
tgcagggtgc agcaggcagc caaattggca tgattgtgaa cagcttcacc aatgtgacag   3180
tggccatgat cattgccttc agcttcagct ggaaactgag ccttgtgatc ctctgcttct   3240
tcccctttct ggccctgtct ggggctaccc agacaagaat gctgactggc tttgcctcca   3300
gagacaagca ggccctggaa atggttggac agatcaccaa tgaggccctg tccaacatca   3360
ggacagtggc aggcattggc aaagagagaa gattcattga ggcccttgag acagagcttg   3420
agaagccctt caagacagcc atccagaaag ctaacatcta tgggttctgc tttgcttttg   3480
cccagtgcat catgttcatt gccaactcag ccagctacag atatggtggc tacctgatct   3540
ctaatgaggg cctgcacttc agctatgtgt tcagagtgat ctctgctgtg gtgctgtctg   3600
```

```
ccactgctct gggcagagcc tttagctaca cccctagcta tgccaaagcc aagatctctg   3660

cagccagatt ctttcagctg ctggatagac agcctcctat cagtgtgtac aacacagctg   3720

gggagaagtg ggacaacttc cagggcaaga ttgactttgt ggattgcaag ttcacctatc   3780

ctagcagacc agactctcag gtgctgaatg gactgagtgt gtctatcagc cctggccaga   3840

cactggcctt tgtgggaagc tctggatgtg gcaagagcac cagcatccag ctgcttgaga   3900

ggttctatga tccagaccag ggcaaagtga tgattgatgg gcatgacagc aagaaagtga   3960

atgtgcagtt cctgaggtcc aacattggga ttgtgtccca agaacctgtt ctgtttgcct   4020

gcagcatcat ggataacatt aagtatgggg acaacaccaa agaaatccct atggaaagag   4080

tgattgctgc agccaagcag gcacagctgc atgattttgt gatgagcctg cctgagaagt   4140

atgagacaaa tgtgggctcc cagggcagcc agctgtctag aggggaaaaa cagagaattg   4200

ccatagccag ggccatagtc agagatccta agattctgct cctggatgag gccacctctg   4260

ctctggatac agagtctgaa aagacagtcc aggtggcact ggacaaggcc agagagggca   4320

gaacctgtat tgtgattgcc cataggctgt ccacaatcca aaatgctgac atcattgcag   4380

tgatggccca aggggttgtg attgagaagg gaacacatga agaactcatg gcccaaaaag   4440

gggcctatta taagctggtc accactggca gccccatcag ctagggatcc atatgatatc   4500

aataaagacc tcttattttc attcatcagg tgtggttggt ttttttgtgt gggggctcga   4560

gatctgagga acccctagtg atggaggcgg ccgcaggaac ccctagtgat ggagttggcc   4620

actccctctc tgcgcgctcg ctcgctcact gaggccgggc gaccaaaggt cgcccgacgc   4680

ccgggctttg cccgggcggc ctcagtgagc gagcgagcgc gcagctgcct gcag         4734
```

```
<210> SEQ ID NO 5
<211> LENGTH: 255
<212> TYPE: DNA
<213> ORGANISM: artificial sequence
<220> FEATURE:
<223> OTHER INFORMATION: Alpha 1 antitrypsin promoter

<400> SEQUENCE: 5

cgccaccccc tccaccttgg acacaggacg ctgtggtttc tgagccaggt acaatgactc     60

ctttcggtaa gtgcagtgga agctgtacac tgcccaggca aagcgtccgg gcagcgtagg    120

cgggcgactc agatcccagc cagtggactt agcccctgtt tgctcctccg ataactgggg    180

tgaccttggt taatattcac cagcagcctc ccccgttgcc cctctggatc cactgcttaa    240

atacggacga ggaca                                                      255
```

```
<210> SEQ ID NO 6
<211> LENGTH: 145
<212> TYPE: DNA
<213> ORGANISM: artificial sequence
<220> FEATURE:
<223> OTHER INFORMATION: Human minimal bile salt export pump (ABCB11)
      gene promoter

<400> SEQUENCE: 6

ttcccaagca cactctgtgt ttggggttat tgctctgagt atgtttctcg tatgtcactg     60

aactgtgctt gggctgccct tagggacatt gatccttagg caaatagata atgttcttga    120

aaaagtttga attctgttca gtgct                                          145
```

```
<210> SEQ ID NO 7
<211> LENGTH: 145
```

<212> TYPE: DNA
<213> ORGANISM: artificial sequence
<220> FEATURE:
<223> OTHER INFORMATION: Mouse minimal Bile Salt export pump (ABCB11)
gene promoter

<400> SEQUENCE: 7
ggttcctgct ttgagtatgt tcgacctttc ctctcatgtc actgaactgt gctagatctg 60
gactttaggc cattgaccta taagcaaata gatagtgttc ttaaaaaagc ctgatttctg 120
ttcaatgctt tattaccatg aaaac 145

<210> SEQ ID NO 8
<211> LENGTH: 56
<212> TYPE: DNA
<213> ORGANISM: artificial sequence
<220> FEATURE:
<223> OTHER INFORMATION: Synthetic poly A sequence

<400> SEQUENCE: 8
aataaagacc tcttattttc attcatcagg tgtggttggt ttttttgtgt gggggc 56

<210> SEQ ID NO 9
<211> LENGTH: 20
<212> TYPE: DNA
<213> ORGANISM: artificial sequence
<220> FEATURE:
<223> OTHER INFORMATION: Forward alpha-1-anti-trypsin promoter primer

<400> SEQUENCE: 9
ttgctcctcc gataactggg 20

<210> SEQ ID NO 10
<211> LENGTH: 20
<212> TYPE: DNA
<213> ORGANISM: artificial sequence
<220> FEATURE:
<223> OTHER INFORMATION: Reverse alpha-1-anti-trypsin promoter primer

<400> SEQUENCE: 10
ccctgtcctc gtccgtattt 20

<210> SEQ ID NO 11
<211> LENGTH: 20
<212> TYPE: DNA
<213> ORGANISM: artificial sequence
<220> FEATURE:
<223> OTHER INFORMATION: Forward wild type BSEP primer

<400> SEQUENCE: 11
tcatccgaaa tcccaagatt 20

<210> SEQ ID NO 12
<211> LENGTH: 19
<212> TYPE: DNA
<213> ORGANISM: artificial sequence
<220> FEATURE:
<223> OTHER INFORMATION: Reverse wild type BSEP primer

<400> SEQUENCE: 12
caagcgatga gcaactgaa 19

<210> SEQ ID NO 13
<211> LENGTH: 20
<212> TYPE: DNA
<213> ORGANISM: artificial sequence -continued

```
<220> FEATURE:
<223> OTHER INFORMATION: Forward codon-optimized BSEP primer

<400> SEQUENCE: 13

taatttccag ggcaagatcg                                          20


<210> SEQ ID NO 14
<211> LENGTH: 20
<212> TYPE: DNA
<213> ORGANISM: artificial sequence
<220> FEATURE:
<223> OTHER INFORMATION: Reverse codon-optimized BSEP primer

<400> SEQUENCE: 14

agcagctgga tagaggtgga                                          20
```

CODON-OPTIMIZED ABCB11 TRANSGENE FOR THE TREATMENT OF PROGRESSIVE FAMILIAL INTRAHEPATIC CHOLESTASIS TYPE 2 (PFIC2)

FIELD OF THE INVENTION

The present disclosure relates to gene therapy vector for use in the treatment of progressive familial intrahepatic cholestasis type 2. More specifically, the present invention relates to an adeno-associated virus vector comprising codon-optimized sequence encoding for the BSEP for the treatment of PFIC2.

BACKGROUND ART

Progressive familial intrahepatic cholestasis 2 (PFIC2) is a genetic disease associated with mutations in the ABCB11 gene which expresses bile salt export pump (BSEP), a 1,321 amino-acids protein with molecular mass of ~160 kDa (Kubitz, R. et al. 2012; Clin Res Hepatol Gas 36(6): 536-553). BSEP is expressed predominantly in the canalicular membranes of hepatocytes and is involved in the transport of bile salts from these cells to the bile (Jacquemin, E. 2012. Clin Res Hepatol Gas 36 Suppl 1: S26-S35). The signs and symptoms of PFIC2 are typically related to liver disease only. People with PFIC2 often develop liver failure within the first few years of life. Additionally, affected individuals are at increased risk of developing hepatocellular carcinoma. PFIC2 causes bile acid to accumulate in the liver leading to decreased bile acids excretion and therefore accumulation in hepatocytes (intrahepatic cholestasis). Cellular bile accumulation leads to hepatocyte death, bile release in blood, severe pruritus, evolution to portal hypertension, liver failure and cirrhosis, and ultimately death in untreated patients. PFIC2 is a rare disease with an estimated incidence of 1 per 100,000 births although the exact prevalence is not known (Gonzales, E. et al. 2014. Eur J Hum Genet 22(4)). The disease affects both genders equally and has been reported from around the world.

There is currently no cure for PFIC2, and therefore the unmet medical need is very high. Although ursodeoxycholic acid (UDCA) therapy may ameliorate symptoms in some patients, outside of liver transplant there is currently no curing treatment for PFIC2 (van der Woerd, W. L et al. World J Gastroentero. 2017; 23(5):763-775). Surgical intervention in the form of biliary diversion improves patient outcomes. However, post-surgical complications such as infections and issues with stoma bags impact patients' quality of life, while the risk of cirrhosis and liver cancer still remains. Liver transplants are an effective treatment, but carry with them the risks involved with such a complicated procedure as well as a chance of re-emergence of the condition. Despite current available treatments, the quality of life and the life expectancy of patients with PFIC2 are still limited.

Gene therapy correcting the defective gene responsible for disease development is a promising treatment for a number of diseases. However, the technique remains still under study. RNA therapy to treat a liver condition such as progressive familial intrahepatic cholestatsis 2 (PFIC2) using various potential therapeutic genes including ABCB11 was only suggested in WO2017/100551 or WO2017/001570. Thus, there is still a need to develop gene therapy methods which allow stable and long-term transgene expression.

Herein, it is described a new type of therapy for PFIC2 based on the delivery to the liver of a codon-optimized version of the ABCB11 gene, by using an adeno-associated virus (AAV) as a vector.

SUMMARY OF THE INVENTION

Surprisingly, the inventors found that contrary to the wild type human BSEP-coding gene (BSEP), the codon optimized sequence of BSEP encoding gene when administered in vivo showed an efficient expression specifically in the canalicular membranes of hepatocytes. In Abcb11$^{-/-}$ knockout mice which reproduce most of PFIC2 symptoms observed in patients, administration of AAV bearing a codon-optimized cDNA versions encoding BSEP achieve a therapeutic effect such as significant decrease of transaminases and restoration of the secretion of bile salts to bile.

A first aspect of the present disclosure thus relates to a nucleic acid construct comprising a transgene encoding BSEP, said transgene is the sequence SEQ ID NO: 1 or a sequence having at least 80% of identity with SEQ ID NO: 1.

In specific embodiments, said nucleic acid construct further comprises a promoter which initiates transgene expression upon introduction into a host cell, preferably a liver specific promoter, more preferably an alpha-1-antitrypsin promoter or a bile salt-inducible promoter.

In specific embodiments, said nucleic acid construct further comprises a 5'ITR (inverted terminal repeat) and a 3'ITR sequences, preferably a 5'ITR and a 3'ITR sequences of adeno-associated virus (AAV), notably a 5'ITR and a 3'ITR sequences from the AAV2 serotype.

In more specific embodiments, said nucleic acid construct comprises or consists of the nucleic acid sequence SEQ ID NO: 3 or a nucleic acid sequence having at least 80% of identity with SEQ ID NO: 3.

In another aspect, said nucleic acid construct is comprised in an expression vector, preferably a viral vector, more preferably an AAV vector.

Another aspect of the present disclosure relates to a viral particle comprising a nucleic acid construct or an expression vector of the invention and preferably comprising capsid proteins of adeno-associated virus such as capsid proteins selected from the group consisting of: AAV3 type 3a, AAV3 type 3B, NP40, NP59, NP84, LK03, AAV3-ST, Anc80 and AAV8 serotype.

Another aspect of the present disclosure relates to a host cell comprising the nucleic acid construct or the expression vector of the invention, or a host cell transduced with a viral particle of the invention.

Another aspect of the present disclosure relates to a pharmaceutical composition comprising the nucleic acid construct, expression vector, host cell, or viral particle of the invention, in combination with one or more pharmaceutical acceptable excipient.

The invention also relates to a product of the invention for use as a medicament, such as the prevention and/or the treatment of progressive familial intrahepatic cholestasis type 2 in a subject in need thereof. In a specific embodiment, the subject is a neonate, an infant, a child or an adult, preferably a neonate, an infant or a child, more preferably a neonate or an infant. Also disclosed herein is a process for producing viral particles as described above, comprising the steps of: a) culturing a host cell as described above in a culture medium, and b) harvesting the viral particles from the cell culture supernatant and/or inside the cells.

The present disclosure also relates to a kit comprising the nucleic acid construct, the expression vector, the host cell, the viral particle, or the pharmaceutical composition as described above, in one or more containers, optionally further comprising instructions or packaging materials.

DETAILED DESCRIPTION

Figure 1:
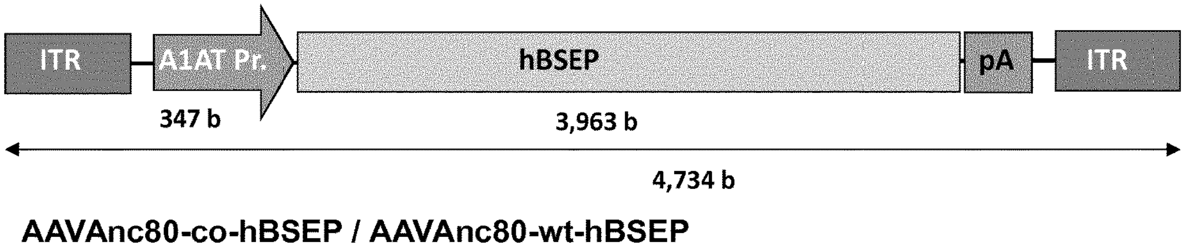
FIG. 1. Diagram of AAVAnc80-wt-hBSEP and AAVAnc80-co-hBSEP vectors used in experiments. A1AT Pr.: A1AT promoter; ITR: inverted terminal repeats; pA: synthetic polyadenylation sequence FIG. 2. Immunofluorescence of cells transfected with AAV plasmids expressing hBSEP. Huh-7 and HepG2 cells were transfected with pAAV-co-hBSEP and pAAV-wt-hB-SEP vectors and analyzed by immunofluorescence with a specific anti-hBSEP antibody after 72 h. Nuclei were stained with DAPI. Magnification: 400×.

The invention relates to a transgene comprising a codon-optimized sequence encoding bile salt export pump (BSEP) (NCBI reference sequence: NP_003733.2). The membrane-associated protein encoded by ABCB11 gene, also named BSEP gene is a member of the superfamily of ATP-binding cassette (ABC) transporters. This gene encodes a liver resident transporter protein which plays an essential role in the enterohepatic circulation of the bile salts. Mutations in this gene cause a form of progressive familial intrahepatic cholestasis which are a group of inherited disorders with severe cholestatic liver disease from early infancy.

As used herein, the term "transgene" refers to exogenous DNA or cDNA encoding a gene product. The gene product may be an RNA, peptide or protein. In addition to the coding region for the gene product, the transgene may include or be associated with one or more elements to facilitate or enhance expression, such as a promoter, enhancer(s), response element(s), reporter element(s), insulator element(s), polyadenylation signal(s) and/or other functional elements. Embodiments of the invention may utilize any known suitable promoter, enhancer(s), response element(s), reporter element(s), insulator element(s), polyadenylation signal(s) and/or other functional elements. Suitable elements and sequences will be well known to those skilled in the art.

Nucleic Acid Construct

More particularly, the invention relates to a nucleic acid construct comprising a transgene encoding BSEP, said transgene is the sequence SEQ ID NO: 1 or 2 or a sequence having at least 80% identity with SEQ ID NO: 1 or 2.

The terms "nucleic acid sequence" and "nucleotide sequence" may be used interchangeably to refer to any molecule composed of or comprising monomeric nucleotides. A nucleic acid may be an oligonucleotide or a polynucleotide. A nucleotide sequence may be a DNA or RNA. A nucleotide sequence may be chemically modified or artificial. Nucleotide sequences include peptide nucleic acids (PNA), morpholinos and locked nucleic acids (LNA), as well as glycol nucleic acids (GNA) and threose nucleic acid (TNA). Each of these sequences is distinguished from naturally-occurring DNA or RNA by changes to the backbone of the molecule. Also, phosphorothioate nucleotides may be used. Other deoxynucleotide analogs include methylphosphonates, phosphoramidates, phosphorodithioates, N3'P5'-phosphoramidates and oligoribonucleotide phosphorothioates and their 2'-0-allyl analogs and 2'-0-methylribonucleotide methylphosphonates which may be used in a nucleotide of the invention.

The term "nucleic acid construct" as used herein refers to a man-made nucleic acid molecule resulting from the use of recombinant DNA technology. A nucleic acid construct is a nucleic acid molecule, either single- or double-stranded, which has been modified to contain segments of nucleic acids sequences, which are combined and juxtaposed in a manner, which would not otherwise exist in nature. A nucleic acid construct usually is a "vector", i.e. a nucleic acid molecule which is used to deliver exogenously created DNA into a host cell.

As used herein, the term "sequence identity" or "identity" refers to the number of matches (identical nucleic acid residues) in positions from an alignment of two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithms (e.g. Needleman and Wunsch algorithm; Needleman and Wunsch, 1970, J Mol Biol.; 48(3):443-53) which aligns the sequences optimally over the entire length, while sequences of substantially different lengths are preferably aligned using a local alignment algorithm (e.g. Smith and Waterman algorithm (Smith and Waterman, 1981, J Theor Biol; 91(2):379-80) or Altschul algorithm (Altschul S F et al., 1997, Nucleic Acids Res; 25(17):3389-402.; Altschul S F et al., 2005, Bioinformatics; 21(8):1451-6)). Alignment for purposes of determining percent nucleic acid sequence identity can be achieved in various ways that are within the skill in the art, for instance, using publicly available computer software available on internet web sites such as http://blast.ncbi.nlm.nih.gov/ or http://www.ebi.ac.uk/Tools/emboss/). Those skilled in the art can determine appropriate parameters for measuring alignment, including any algorithms needed to achieve maximal alignment over the full length of the sequences being compared. For purposes herein, % nucleic acid sequence identity values refers to values generated using the pair wise sequence alignment program EMBOSS Needle that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

As used herein, said nucleic acid construct comprises a transgene encoding BSEP according to the invention and one or more control sequence required for expression of said coding sequence. Generally, the nucleic acid construct comprises a coding sequence and regulatory sequences preceding (5' non-coding sequences) and following (3' non-coding sequences) the coding sequence that are required for expression of the selected gene product. Thus, a nucleic acid construct typically comprises a promoter sequence, a coding sequence and a 3' untranslated region that usually contains a polyadenylation site and/or transcription terminator. The nucleic acid construct may also comprise additional regulatory elements such as, for example, enhancer sequences, a polylinker sequence facilitating the insertion of a DNA fragment within a vector and/or splicing signal sequences.

In one embodiment, the nucleic acid construct comprises a promoter. Said promoter initiates transgene expression upon introduction into a host cell. As used herein, the term "promoter" refers to a regulatory element that directs the transcription of a nucleic acid to which it is operably linked. A promoter can regulate both rate and efficiency of transcription of an operably linked nucleic acid. A promoter may also be operably linked to other regulatory elements which enhance ("enhancers") or repress ("repressors") promoter-dependent transcription of a nucleic acid. These regulatory elements include, without limitation, transcription factor binding sites, repressor and activator protein binding sites, and any other sequences of nucleotides known to one of skill in the art to act directly or indirectly to regulate the amount of transcription from the promoter, including e.g. attenuators, enhancers, and silencers. The promoter is located near the transcription start site of the gene or coding sequence to which it is operably linked, on the same strand and upstream of the DNA sequence (towards the 5' region of the sense strand). A promoter can be about 100-1000 base pairs long. Positions in a promoter are designated relative to the transcriptional start site for a particular gene (i.e., positions upstream are negative numbers counting back from −1, for example −100 is a position 100 base pairs upstream).

As used herein, the term "operably linked" refers to a linkage of polynucleotide (or polypeptide) elements in a functional relationship. A nucleic acid is "operably linked" when it is placed into a functional relationship with another nucleic acid sequence. For instance, a promoter or transcription regulatory sequence is operably linked to a coding sequence if it affects the transcription of the coding sequence. Operably linked means that the DNA sequences being linked are typically contiguous; where it is necessary to join two protein encoding regions, they are contiguous and in reading frame.

In a particular embodiment, the nucleic acid construct of the invention further comprises a liver-specific promoter operably-linked to the transgene of the invention. In the context of this invention, a "liver-specific promoter" is a promoter which is more active in the liver than in any other tissue of the body. Typically, the activity of a liver specific promoter will be considerably greater in the liver than in other tissues. For example, such a promoter may be at least 2, at least 3, at least 4, at least 5 or at least 10 times more active (for example as determined by its ability to drive the expression in a given tissue in comparison to its ability to drive the expression in other cells or tissues). Accordingly, a liver specific promoter allows an active expression in the liver of the gene linked to it and prevents its expression in other cells or tissues.

In one embodiment, the liver-specific promoter comprises a nucleotide sequence of the α1-antitrypsin gene promoter (AAT or A1AT) (SEQ ID NO: 5), a bile salt-inducible promoter (SEQ ID NO: 6 or 7) or a chimeric promoter sequence EalbPa1AT that comprises a α1-antitrypsin gene promoter sequence (AAT or Pa1AT) combined with an albumin gene enhancer element (Ealb). All these promoter sequences have properties of liver specific promoters.

Each of these nucleic acid construct embodiments may also include a polyadenylation signal sequence; together or not with other optional nucleotide elements. As used herein, the term "polyadenylation signal" or "poly(A) signal" refers to a specific recognition sequence within 3' untranslated region (3' UTR) of the gene, which is transcribed into precursor mRNA molecule and guides the termination of the gene transcription. Poly(A) signal acts as a signal for the endonucleolytic cleavage of the newly formed precursor mRNA at its 3'-end, and for the addition to this 3'-end of a RNA stretch consisting only of adenine bases (polyadenylation process; poly(A) tail). Poly(A) tail is important for the nuclear export, translation, and stability of mRNA. In the context of the invention, the polyadenylation signal is a recognition sequence that can direct polyadenylation of mammalian genes and/or viral genes, in mammalian cells.

Poly(A) signals typically consist of a) a consensus sequence AAUAAA, which has been shown to be required for both 3'-end cleavage and polyadenylation of premessenger RNA (pre-mRNA) as well as to promote downstream transcriptional termination, and b) additional elements upstream and downstream of AAUAAA that control the efficiency of utilization of AAUAAA as a poly(A) signal. There is considerable variability in these motifs in mammalian genes.

In one embodiment, the polyadenylation signal sequence of the nucleic acid construct of the invention is a polyadenylation signal sequence of a mammalian gene or a viral gene. Suitable polyadenylation signals include, among others, a SV40 early polyadenylation signal, a SV40 late polyadenylation signal, a HSV thymidine kinase polyadenylation signal, a protamine gene polyadenylation signal, an adenovirus 5 EIb polyadenylation signal, a growth hormone polydenylation signal, a PBGD polyadenylation signal, in silico designed polyadenylation signal (synthetic) and the like.

In a particular embodiment, the polyadenylation signal sequence of the nucleic acid construct is a synthetic poly(A) signal sequence based on the rabbit beta-globin gene, more particularly a synthetic poly(A) having sequence SEQ ID NO: 8.

Expression Vector

The nucleic acid construct of the invention may be comprised in an expression vector. As used herein, the term "expression vector" refers to a nucleic acid molecule used as a vehicle to transfer genetic material, and in particular to deliver a nucleic acid into a host cell, either in vitro or in vivo. Expression vector also refers to a nucleic acid molecule capable of effecting expression of a gene (transgene) in host cells or host organisms compatible with such sequences. Expression vectors typically include at least suitable transcription regulatory sequences and optionally 3'-transcription termination signals. Additional factors necessary or helpful in effecting expression may also be present, such as expression enhancer elements able to respond to a precise inductive signal (endogenous or chimeric transcription factors) or specific for certain cells, organs or tissues. Vectors include, but are not limited to, plasmids, phasmids, cosmids, transposable elements, viruses, and artificial chromosomes (e.g., YACs). Preferably, the vector of the invention is a vector suitable for use in gene or cell therapy, and in particular is suitable to target liver cells.

In some embodiments, the expression vector is a viral vector, such as vectors derived from Moloney murine leukemia virus vectors (MoMLV), MSCV, SFFV, MPSV or SNV, lentiviral vectors (e.g. derived from human immunodeficiency virus (HIV), simian immunodeficiency virus (SIV), feline immunodeficiency virus (FIV), bovine immunodeficiency virus (BIV) or equine infectious anemia virus (EIAV)), adenoviral (Ad) vectors, adeno-associated viral (AAV) vectors, simian virus 40 (SV-40) vectors, bovine papilloma virus vectors, Epstein-Barr virus, herpes virus vectors, vaccinia virus vectors, Harvey murine sarcoma virus vectors, murine mammary tumor virus vectors, Rous sarcoma virus vectors.

As is known in the art, depending on the specific viral vector considered for use, suitable sequences should be introduced in the vector of the invention for obtaining a functional viral vector, such as AAV ITRs for an AAV vector, or LTRs for lentiviral vectors. In a particular embodiment, said vector is an AAV vector.

AAV has arisen considerable interest as a potential vector for human gene therapy. Among the favourable properties of the virus are its lack of association with any human disease, its ability to infect both dividing and non-dividing cells, and the wide range of cell lines derived from different tissues that can be infected. The AAV genome is composed of a linear, single-stranded DNA molecule which contains 4681 bases (Berns and Bohenzky, 1987, Advances in Virus Research (Academic Press, Inc.) 32:243-307). The genome includes inverted terminal repeats (ITRs) at each end, which function in cis as origins of DNA replication and as packaging signals for the virus. The ITRs are approximately 145 bp in length. The internal non-repeated portion of the genome includes two large open reading frames, known as the AAV rep and cap genes, respectively. These genes code for the viral proteins involved in replication and packaging of the virion. In particular, at least four viral proteins are synthesized from the AAV rep gene, Rep 78, Rep 68, Rep 52 and Rep 40, named according to their apparent molecular weight. The AAV cap gene encodes at least three proteins, VP1, VP2 and VP3. For a detailed description of the AAV genome, see, e.g., Muzyczka, N. 1992 Current Topics in Microbiol. and Immunol. 158:97-129.

Thus, in one embodiment, the nucleic acid construct or expression vector comprising transgene of the invention further comprises a 5'ITR and a 3'ITR sequences, preferably a 5'ITR and a 3' ITR sequences of an adeno-associated virus.

As used herein the term "inverted terminal repeat (ITR)" refers to a nucleotide sequence located at the 5'-end (5'ITR) and a nucleotide sequence located at the 3'-end (3'ITR) of a virus, that contain palindromic sequences and that can fold over to form T-shaped hairpin structures that function as primers during initiation of DNA replication. They are also needed for viral genome integration into the host genome; for the rescue from the host genome; and for the encapsidation of viral nucleic acid into mature virions. The ITRs are required in cis for the vector genome replication and its packaging into the viral particles.

AAV ITRs for use in the viral vector of the invention may have a wild-type nucleotide sequence or may be altered by the insertion, deletion or substitution. The serotype of the inverted terminal repeats (ITRs) of the AAV may be selected from any known human or nonhuman AAV serotype. In specific embodiments, the nucleic acid construct or viral expression vector may be carried out by using ITRs of any AAV serotype, including AAV1, AAV2, AAV3 (including types 3A and 3B), AAV4, AAV5, AAV6, AAV7, AAV8, AAV9, AAV10, AAV11, AAV12, avian AAV, bovine AAV, canine AAV, equine AAV, ovine AAV, and any other AAV serotype now known or later discovered.

In one embodiment, the nucleic acid construct further comprises a 5'ITR and a 3'ITR of an AAV of a serotype AAV2.

In a particular embodiment, the nucleic acid construct of the invention comprises or consists of SEQ ID NO: 3 or 4 or a sequence having at least 80% of identity with SEQ ID NO: 3 or 4.

In one embodiment, the nucleic acid construct or AAV vector genome according to the invention is comprised in a recombinant baculovirus genome. As used herein, the term "recombinant baculovirus genome" refers to a nucleic acid that comprises baculoviral genetic elements for autonomous replication of a recombinant baculovirus genome in a host cell permissive for baculovirus infection and replication, typically insect cells. The term "recombinant baculovirus genome" expressly includes genomes comprising nucleic acids that are heterologous to the baculovirus. Likewise, the term "recombinant baculovirus genome" does not necessarily refer to a complete baculovirus genome as the genome may lack viral sequences that are not necessary for completion of an infection cycle. In particular, the recombinant baculovirus genomes may include the heterologous AAV genes useful for rAAV production and/or the transgene such as codon-optimized BSEP cDNA to be encapsidated in the rAAV for use in gene therapy. The baculoviral genetic elements for use in the present disclosure are preferably obtained from AcMNPV baculovirus (*Autographa californica* multinucleocapsid nucleopolyhedrovirus).

In a particular embodiment, the genes encoding baculovirus cathepsin and chitinase in said first and second baculoviral genomes are disrupted or deleted. In particular, the genes v-cath (Ac127) and chiA (Ac126) of the AcMNPV baculovirus may be disrupted or deleted so that the corresponding cathepsin or chitinase are either not expressed or expressed as inactive forms (i.e. have no enzymatic cathepsin or chitinase activity). In a particular embodiment, said recombinant baculovirus genomes are further disrupted or deleted for at least p24 gene (Ac129), preferably for the three baculoviral genes p10 (Ac137), p24 and p26 (Ac136). In a particular embodiment, said recombinant baculovirus genomes include functional p74 baculoviral gene (Ac138) (i.e. said gene has not been deleted or disrupted).

On the other hand, the nucleic acid construct or expression vector of the invention can be carried out by using synthetic 5'ITR and/or 3'ITR; and also by using a 5'ITR and a 3'ITR which come from viruses of different serotypes. All other viral genes required for viral vector replication can be provided in trans within the virus-producing cells (packaging cells) as described below. Therefore, their inclusion in the viral vector is optional.

In one embodiment, the nucleic acid construct or viral vector of the invention comprises a 5'ITR, a ψ packaging signal, and a 3'ITR of a virus. "ψ packaging signal" is a cis-acting nucleotide sequence of the virus genome, which in some viruses (e.g. adenoviruses, lentiviruses . . . ) is essential for the process of packaging the virus genome into the viral capsid during replication.

The construction of recombinant AAV viral particles is generally known in the art and has been described for instance in U.S. Pat. Nos. 5,173,414 and 5,139,941; WO 92/01070, WO 93/03769, Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Current Topics in Microbiol. and Immunol. 158:97-129; and Kotin, R. M. (1994) Human Gene Therapy 5:793-801.

Viral Particle

The nucleic acid construct or the expression vector of the invention may be packaged into a virus capsid to generate a "viral particle", also named "viral vector particle". In a particular embodiment, the nucleic acid construct or the expression vector of the invention is packaged into an AAV-derived capsid to generate an "adeno-associated viral particle" or "AAV particle". The present invention relates to a viral particle comprising a nucleic acid construct or an expression vector of the invention and preferably comprising capsid proteins of adeno-associated virus.

The term AAV vector particle encompasses any recombinant AAV vector particle or mutant AAV vector particle, genetically engineered. A recombinant AAV particle may be prepared by encapsidating the nucleic acid construct or viral expression vector including ITR(s) derived from a particular AAV serotype on a viral particle formed by natural or mutant Cap proteins corresponding to an AAV of the same or different serotype.

Proteins of the viral capsid of an adeno-associated virus include the capsid proteins VP1, VP2, and VP3. Differences among the capsid protein sequences of the various AAV serotypes result in the use of different cell surface receptors for cell entry. In combination with alternative intracellular processing pathways, this gives rise to distinct tissue tropisms for each AAV serotype.

Several techniques have been developed to modify and improve the structural and functional properties of naturally occurring AAV viral particles (Bünning H et al. J Gene Med, 2008; 10: 717-733; Paulk et al. Mol ther. 2018; 26(1):289-303; Wang L et al. Mol Ther. 2015; 23(12):1877-87; Vercauteren et al. Mol Ther. 2016; 24(6):1042-1049; Zinn E et al., Cell Rep. 2015; 12(6):1056-68).

Thus, in AAV viral particle according to the present disclosure, the nucleic acid construct or viral expression vector including ITR(s) of a given AAV serotype can be packaged, for example, into: a) a viral particle constituted of capsid proteins derived from the same or different AAV serotype [e.g. AAV2 ITRs and AAV5 capsid proteins; AAV2 ITRs and AAV8 capsid proteins; AAV2 ITRs and Anc80 capsid proteins; AAV2 ITRs and AAV9 capsid proteins]; b) a mosaic viral particle constituted of a mixture of capsid proteins from different AAV serotypes or mutants [e.g. AAV2 ITRs with AAV1 and AAV5 capsid proteins]; c) a chimeric viral particle constituted of capsid proteins that have been truncated by domain swapping between different AAV serotypes or variants [e.g. AAV2 ITRs with AAV5 capsid proteins with AAV3 domains].

The skilled person will appreciate that the AAV viral particle for use according to the present disclosure may comprise capsid proteins from any AAV serotype including AAV1, AAV2, AAV3 (including types 3A and 3B), AAV4, AAV5, AAV6, AAV7, AAV8, AAV9, AAV10, AAV11, AAV12, avian AAV, bovine AAV, canine AAV, equine AAV, ovine AAV, synthetic AAV variants such as NP40, NP59, NP84 (Paulk et al. Mol ther. 2018.26(1):289-303), LK03 (Wang L et al. Mol Ther. 2015. 23(12):1877-87), AAV3-ST (Vercauteren et al. Mol Ther. 2016.24(6):1042-1049), Anc80 (Zinn E et al., Cell Rep. 2015; 12(6):1056-68) and any other AAV serotype now known or later discovered.

In a specific embodiment, the AAV viral particle comprises capsid proteins from a serotype selected from the group consisting of an AAV1, AAV3B, an AAV5, an AAV7, an AAV8, and an AAV9 which are more suitable for delivery to the liver cells (Nathwani et al. Blood 2007; 109: 1414-1421; Kitajima et al. Atherosclerosis 2006; 186:65-73).

In a particular embodiment, the AAV viral particle comprises capsid proteins from Anc80, a predicted ancestor of viral AAVs serotypes 1, 2, 8, and 9 that behaves as a highly potent gene therapy vector for targeting liver, muscle and retina (Zinn E et al., Cell Rep. 2015; 12(6):1056-68). In a more particular embodiment, the viral particle comprises the Anc80L65 VP3 capsid protein (Genbank accession number: KT235804).

Thus, in a further aspect, the present invention relates to a viral particle comprising a nucleic acid construct or expression vector of the invention and preferably comprising capsid proteins of adeno-associated virus such as capsid proteins from Anc80.

In a particular embodiment, the viral particle comprises AAV vector genome comprised in recombinant baculovirus. Thus, a second recombinant baculovirus genome comprising AAV rep and cap is used for producing AAV viral particle. In a particular embodiment, the rep and cap proteins are expressed from distinct baculovirus late promoters, preferably in inverse orientation. In a specific embodiment, that may be combined with the previous embodiments, the second baculovirus genome include a heterologous nucleic acid encoding the rep proteins, for example, rep proteins from AAV2 under the transcriptional control of the baculovirus polyhedron ($P_{Ph}$) promoter. In other embodiment, the second baculovirus genome includes a heterologous nucleic acid encoding the cap proteins under the transcriptional control of the p10 baculovirus promoter. Other modifications of the wild-type AAV sequences for proper expression in insect cells and/or to increase yield of VP and virion or to alter tropism or reduce antigenicity of the virion are also known in the art. By using helper baculoviral construct encoding the rep ORF (open reading frame) of an AAV serotype and cap ORF of a different serotype AAV, it is feasible packaging a vector flanked by ITRs of a given AAV serotype into virions assembled from structural capsid proteins of a different serotype. It is also possible by this same procedure to package mosaic, chimeric or targeted vectors.

Virus-glycan interactions are critical determinants of host cell invasion. In a particular embodiment, the AAV viral particle comprises capsid proteins comprising one or more amino acids substitutions, wherein the substitutions introduce a new glycan binding site into the AAV capsid protein. In a more particular embodiment, the amino acid substitutions are in amino acid 266, amino acids 463-475 and amino acids 499-502 in AAV2 or the corresponding amino acid positions in AAV1, AAV3, AAV4, AAV5, AAV6, AAV7, AAV 8, AAV9, AAV10 or any other AAV serotype, also included Anc80 and Anc80L65.

The introduced new glycan binding site can be a hexose binding site [e.g. a galactose (Gal), a mannose (Man), a glucose (Glu) or a fucose (fuc) binding site]; a sialic acid (Sia) binding site [e.g. a Sia residue such as is N-acetylneuraminic acid (NeuSAc) or N-Glycolylneuraminic acid (NeuSGc)]; or a disaccharide binding site, wherein the disaccharide is a sialic acid linked to galactose, for instance in the form of Sia(alpha2,3)Gal or Sia(alpha2,6)Gal. Detailed guidance to introduce a new binding site from an AAV serotype into a capsid protein of an AAV of another serotype is given on international patent publication WO2014144229 and in Shen et al. (J. Biol. Chem. 2013; 288(40):28814-28823). In a particular embodiment, the Gal binding site from AAV9 is introduced into the AAV2 VP3 backbone resulting in a dual glycan-binding AAV strain which is able to use both HS and Gal receptors for cell entry. Preferably, said dual glycan-binding AAV strain is AAV2G9. Shen et al. generated AAV2G9 by substituting amino acid residues directly involved and immediately flanking the Gal recognition site on the AAV9 VP3 capsid protein subunit onto corresponding residues on the AAV2 VP3 subunit coding region (AAV2 VP3 numbering Q464V, A467P, D469N, I470M, R471A, D472V, S474G, Y500F, and S501A).

In another embodiment, the viral particle for use according to the present disclosure may be an adenoviral particle, such as an Ad5 viral particle. As it is the case for AAV viral particle, capsid proteins of Ad viral particles can also be engineered to modify their tropism and cellular targeting properties, alternative adenoviral serotypes can also be employed.

A Process for Producing Viral Particles

Production of viral particles carrying the expression viral vector as disclosed above can be performed by means of conventional methods and protocols, which are selected taking into account the structural features chosen for the actual embodiment of expression vector and viral particle of the vector to be produced.

Briefly, viral particles can be produced in a host cell, more particularly in specific virus-producing cell (packaging cell), which is transfected with the nucleic acid construct or expression vector to be packaged, in the presence of a helper vector or virus or other DNA construct(s).

The term "packaging cells" as used herein, refers to a cell or cell line which may be transfected with a nucleic acid construct or expression vector of the invention and provides in trans all the missing functions which are required for the complete replication and packaging of a viral vector. Typically, the packaging cells express in a constitutive or inducible manner one or more of said missing viral functions. Said packaging cells can be adherent or suspension cells.

Typically, a process of producing viral particles comprises the following steps:

a) culturing a packaging cell comprising a nucleic acid construct or expression vector as described above in a culture medium; and b) harvesting the viral particles from the cell culture supernatant and/or inside the cells.

Conventional methods can be used to produce AAV viral particles which consist on transient cell co-transfection with nucleic acid construct or expression vector (e.g. a plasmid) carrying the transgene of the invention; a nucleic acid construct (e.g., an AAV helper plasmid) that encodes rep and cap genes, but does not carry ITR sequences; and with a third nucleic acid construct (e.g., a plasmid) providing the adenoviral functions necessary for AAV replication.

Viral genes necessary for AAV replication are referred herein as viral helper genes. Typically, said genes necessary for AAV replication are adenoviral helper genes, such as E1A, E1B, E2a, E4, or VA RNAs. Preferably, the adenoviral helper genes are of the Ad5 or Ad2 serotype.

Large-scale production of AAV particles according to the disclosure can also be carried out for example by infection of insect cells with a combination of recombinant baculoviruses (Urabe et al. Hum. Gene Ther. 2002; 13: 1935-1943). SF9 cells are co-infected with two or three baculovirus vectors respectively expressing AAV rep, AAV cap and the AAV vector to be packaged. The recombinant baculovirus vectors will provide the viral helper gene functions required for virus replication and/or packaging. Smith et al 2009 (Molecular Therapy, vol. 17, no. 11, pp 1888-1896) further describes a dual baculovirus expression system for large-scale production of AAV particles in insect cells.

Suitable culture media will be known to a person skilled in the art. The ingredients that compose such media may vary depending on the type of cell to be cultured. In addition to nutrient composition, osmolarity and pH are considered important parameters of culture media. The cell growth medium comprises a number of ingredients well known by the person skilled in the art, including amino acids, vitamins, organic and inorganic salts, sources of carbohydrate, lipids, trace elements (CuS04, FeS04, Fe(N03)3, ZnS04 . . . ), each ingredient being present in an amount which supports the cultivation of a cell in vitro (i.e., survival and growth of cells). Ingredients may also include different auxiliary substances, such as buffer substances (like sodium bicarbonate, Hepes, Tris . . . ), oxidation stabilizers, stabilizers to counteract mechanical stress, protease inhibitors, animal growth factors, plant hydrolyzates, anti-clumping agents, anti-foaming agents. Characteristics and compositions of the cell growth media vary depending on the particular cellular requirements. Examples of commercially available cell growth media are: MEM (Minimum Essential Medium), BME (Basal Medium Eagle) DMEM (Dulbecco's modified Eagle's Medium), Iscoves DMEM (Iscove's modification of Dulbecco's Medium), GMEM, RPMI 1640, Leibovitz L-15, McCoy's, Medium 199, Ham (Ham's Media) F10 and derivatives, Ham F12, DMEM/F12, etc.

Further guidance for the construction and production of viral vectors for use according to the disclosure can be found in Viral Vectors for Gene Therapy, Methods and Protocols. Series: Methods in Molecular Biology, Vol. 737. Merten and Al-Rubeai (Eds.); 2011 Humana Press (Springer); Gene Therapy. M. Giacca. 2010 Springer-Verlag; Heilbronn R. and Weger S. Viral Vectors for Gene Transfer: Current Status of Gene Therapeutics. In: Drug Delivery, Handbook of Experimental Pharmacology 197; M. Schafer-Korting (Ed.). 2010 Springer-Verlag; pp. 143-170; Adeno-Associated Virus: Methods and Protocols. R. O. Snyder and P. Moulllier (Eds). 2011 Humana Press (Springer); Bünning H. et al. Recent developments in adeno-associated virus technology. J. Gene Med. 2008; 10:717-733; Adenovirus: Methods and Protocols. M. Chillón and A. Bosch (Eds.); Third Edition. 2014 Humana Press (Springer)

Host Cells

In another aspect, the invention relates to a host cell comprising a nucleic acid construct or an expression vector of the invention. More particularly, host cell according to the invention is a specific virus-producing cell, also named packaging cell which is transfected with the nucleic acid construct or expression vector according to the invention, in the presence of a helper vector or virus or other DNA constructs and provides in trans all the missing functions which are required for the complete replication and packaging of a viral particle. Said packaging cells can be adherent or suspension cells For example, said packaging cells may be eukaryotic cells such as mammalian cells, including simian, human, dog and rodent cells. Examples of human cells are PER.C6 cells (WO01/38362), MRC-5 (ATCC CCL-171), WI-38 (ATCC CCL-75), HEK-293 cells (ATCC CRL-1573), HeLa cells (ATCC CCL2) and fetal rhesus lung cells (ATCC CL-160). Examples of non-human primate cells are Vero cells (ATCC CCL81), COS-1 cells (ATCC CRL-1650) or COS-7 cells (ATCC CRL-1651). Examples of dog cells are MDCK cells (ATCC CCL-34). Examples of rodent cells are hamster cells, such as BHK21-F, HKCC cells, or CHO cells.

As an alternative to mammalian sources, the packaging cells for producing the viral particles may be derived from avian sources such as chicken, duck, goose, quail or pheasant. Examples of avian cell lines include avian embryonic stem cells (WO01/85938 and WO03/076601), immortalized duck retina cells (WO2005/042728), and avian embryonic stem cell derived cells, including chicken cells (WO2006/108846) or duck cells, such as EB66 cell line (WO2008/129058 & WO2008/142124).

In another embodiment, the cells can be any cells permissive for baculovirus infection and replication packaging cells. In a particular embodiment, said cells are insect cells, such as SF9 cells (ATCC CRL-1711), Sf21 cells (IPLB-Sf21), MG1 cells (BTI-TN-MG1) or High Five™ cells (BTI-TN-5B1-4).

Accordingly, in a particular embodiment, the host cell comprises:

- a nucleic acid construct or expression vector comprising a transgene encoding BSEP according to the invention (e.g., the AAV vector according to the invention),
- a nucleic acid construct, for example a plasmid, encoding AAV rep and/or cap genes which does not carry the ITR sequences; and/or
- a nucleic acid construct, for example a plasmid or virus, comprising viral helper genes.

In another aspect, the invention relates to a host cell transduced with a viral particle of the invention and the term "host cell" as used herein refers to any cell line that is susceptible to infection by a virus of interest, and amenable to culture in vitro.

The host cell of the invention may be used for ex vivo gene therapy purposes. In such embodiments, the cells are transduced with the viral particle of the invention and subsequently transplanted to the patient or subject. Transplanted cells can have an autologous, allogenic or heterologous origin. For clinical use, cell isolation will generally be carried out under Good Manufacturing Practices (GMP) conditions. Before transplantation, cell quality and absence of microbial or other contaminants is typically checked and liver preconditioning, such as with radiation and/or an immunosuppressive treatment, may be carried out. Furthermore, the host cells may be transplanted together with growth factors to stimulate cell proliferation and/or differentiation, such as Hepatocyte Growth Factor (HGF).

In a particular embodiment, the host cell is used for ex vivo gene therapy into the liver. Preferably, said cells are eukaryotic cells such as mammalian cells, these include, but are not limited to, humans, non-human primates such as apes; chimpanzees; monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like. A person skilled in the art will choose the more appropriate cells according to the patient or subject to be transplanted.

Said host cell may be a cell with self-renewal and pluripotency properties, such as stem cells or induced pluripotent stem cells. Stem cells are preferably mesenchymal stem cells. Mesenchymal stem cells (MSCs) are capable of differentiating into at least one of an osteoblast, a chondrocyte, an adipocyte, or a myocyte and may be isolated from any type of tissue. Generally MSCs will be isolated from bone marrow, adipose tissue, umbilical cord, or peripheral blood. Methods for obtaining thereof are well known to a person skilled in the art. Induced pluripotent stem cells (also known as iPS cells or iPSCs) are a type of pluripotent stem cell that can be generated directly from adult cells. Yamanaka et al. induced iPS cells by transferring the Oct3/4, Sox2, Klf4 and c-Myc genes into mouse and human fibroblasts, and forcing the cells to express the genes (WO 2007/069666). Thomson et al. subsequently produced human iPS cells using Nanog and Lin28 in place of Klf4 and c-Myc (WO 2008/118820).

Said host cells may also be hepatocytes. Hepatocyte transplantation procedures, including cell isolation and subsequent transplantation into a human or mice recipient is described for instance in Filippi and Dhawan, Ann NY Acad Sci. 2014, 1315 50-55; Yoshida et al., Gastroenterology 1996, 111: 1654-1660; Irani et al. Molecular Therapy 2001, 3:3, 302-309; and Vogel et al. J Inherit Metab Dis 2014, 37:165-176. A method for ex vivo transduction of a viral particle into hepatocytes is described for instance in Merle et al., Scandinavian Journal of Gastroenterology 2006, 41:8, 974-982.

Pharmaceutical Compositions

Another aspect of the present disclosure relates to a pharmaceutical composition comprising a nucleic acid construct, an expression vector, a viral particle or a host cell of the invention in combination with one or more pharmaceutical acceptable excipient, diluent or carrier.

As used herein, the term "pharmaceutically acceptable" means approved by a regulatory agency or recognized pharmacopeia such as European Pharmacopeia, for use in animals and/or humans. The term "excipient" refers to a diluent, adjuvant, carrier, or vehicle with which the therapeutic agent is administered.

Any suitable pharmaceutically acceptable carrier, diluent or excipient can be used in the preparation of a pharmaceutical composition (See e.g., Remington: The Science and Practice of Pharmacy, Alfonso R. Gennaro (Editor) Mack Publishing Company, April 1997). Pharmaceutical compositions are typically sterile and stable under the conditions of manufacture and storage. Pharmaceutical compositions may be formulated as solutions (e.g. saline, dextrose solution, or buffered solution, or other pharmaceutically acceptable sterile fluids), microemulsions, liposomes, or other ordered structure suitable to accommodate a high product concentration (e.g. microparticles or nanoparticles). The carrier may be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition.

Prolonged absorption of the injectable compositions can be brought about by including in the composition an agent which delays absorption, for example, monostearate salts and gelatin. The product of the invention may be administered in a controlled release formulation, for example in a composition which includes a slow release polymer or other carriers that protect the product against rapid release, including implants and microencapsulated delivery systems. Biodegradable and biocompatible polymers may for example be used, such as ethylene vinyl acetate, polyanhydrides, polyglycolic acid, collagen, polyorthoesters, polylactic acid and polylactic/polyglycolic copolymers (PLG). Preferably, said pharmaceutical composition is formulated as a solution, more preferably as an optionally buffered saline solution. Supplementary active compounds can also be incorporated into the pharmaceutical compositions of the invention. Guidance on co-administration of additional therapeutics can for example be found in the Compendium of Pharmaceutical and Specialties (CPS) of the Canadian Pharmacists Association.

In one embodiment, the pharmaceutical composition is a parenteral pharmaceutical composition, including a composition suitable for intravenous, intraarterial, subcutaneous, intraperitoneal or intramuscular administration. These pharmaceutical compositions are exemplary only and do not limit the pharmaceutical compositions suitable for other parenteral and non-parenteral administration routes. The pharmaceutical compositions described herein can be packaged in single unit dosage or in multidosage forms.

Therapeutic Uses

In a further aspect, the invention relates to a nucleic acid construct, expression vector, viral particle, host cell or pharmaceutical composition of the invention for use as a medicament in a subject in need thereof.

The term "subject" or "patient" as used herein, refers to mammals. Mammalian species that can benefit from the disclosed methods of treatment include, but are not limited to, humans, non-human primates such as apes, chimpanzees, monkeys, and orangutans, domesticated animals, including dogs and cats, as well as livestock such as horses, cattle, pigs, sheep, and goats, or other mammalian species including, without limitation, mice, rats, guinea pigs, rabbits, hamsters, and the like. In particular embodiment, said subject is neonate, an infant or, a child, more particularly a neonate or an infant. As used herein "neonate" refers to a baby who is less than 28 days and "infants" as used herein refers to a child who is between 29 days and 2 years.

In an additional aspect, the invention relates to a nucleic acid construct, expression vector, viral particle, host cell or pharmaceutical composition of the invention for use in the treatment of a liver disease, in particular progressive familial intrahepatic cholestasis type 2 (PFIC2) in a subject in need thereof.

As used herein, the term "treatment", "treat" or "treating" refers to any act intended to ameliorate the health status of patients such as therapy, prevention, prophylaxis and retardation of the disease. In certain embodiments, such term refers to the amelioration or eradication of a disease or symptoms associated with a disease. According to the present invention, examples of symptoms associated with PFIC2 are hepatocyte death, decreased bile flow and accumulation of bile salts inside the hepatocyte and in blood, severe pruritus, permanent jaundice, evolution to portal hypertension, liver failure and cirrhosis. In other embodiments, this term refers to minimizing the spread or worsening of the disease resulting from the administration of one or more therapeutic agents to a subject with such a disease.

In a particular embodiment, liver disease is selected from the group consisting of: PFIC2, BRIC-2 (benign recurrent intrahepatic cholestasis type 2) or ICP (Intrahepatic cholestasis of pregnancy), drug induced cholestasis and transient neonatal cholestasis.

In a more particular embodiment, said liver disease is PFIC2.

In a related aspect, the invention pertains to the use of a nucleic acid construct, expression vector, viral particle, host cell or pharmaceutical composition of the invention in the preparation of a medicament for use in the treatment of a liver disease, preferably for use in the treatment of PFIC2.

In a further aspect, the invention relates to a method of treating and/or preventing a liver disease, preferably PFIC2, in a subject in need thereof that comprises administering to the subject a therapeutically effective amount of a nucleic acid construct, expression vector, viral particle, host cell or pharmaceutical composition of the invention.

In the context of the invention, an "effective amount" means a therapeutically effective amount.

As used herein a "therapeutically effective amount" refers to an amount effective, at dosages and for periods of time necessary to achieve the desired therapeutic result, such as amelioration or restoration of secretion of bile salts to bile. The therapeutically effective amount of the product of the invention, or pharmaceutical composition that comprises it may vary according to factors such as the disease state, age, sex, and weight of the individual, and the ability of the product or pharmaceutical composition to elicit a desired response in the individual. Dosage regimens may be adjusted to provide the optimum therapeutic response. A therapeutically effective amount is also typically one in which any toxic or detrimental effect of the product or pharmaceutical composition is outweighed by the therapeutically beneficial effects.

The treatment with a product of the invention may alleviate, ameliorate, or reduce the severity of one or more symptoms of PFIC2. For example, treatment may increase and/or restore secretion of bile salts to bile; decrease the amount of bile salts in liver and blood, decrease pruritus, decrease liver damage reducing transaminase levels in serum, and as a consequence may alleviate, ameliorate, or reduce the severity of the disease The product of the invention will be typically included in a pharmaceutical composition or medicament, optionally in combination with a pharmaceutical carrier, diluent and/or adjuvant. Such composition or medicinal product comprises the product of the invention in an effective amount, sufficient to provide a desired therapeutic effect, and a pharmaceutically acceptable carrier or excipient.

In one embodiment the nucleic acid construct, expression vector, viral particle, host cell or pharmaceutical composition for its therapeutic use is administered to the subject or patient by a parenteral route, in particularly by intravenous, intraarterial, subcutaneous, intraperitoneal, or intramuscular route.

In one embodiment, the nucleic acid construct, expression vector, viral particle, host cell or pharmaceutical composition for its therapeutic use is administered by interstitial route, i.e. by injection to or into the interstices of a tissue. The tissue target may be specific, for example the liver tissue, or it may be a combination of several tissues, for example the muscle and liver tissues. Exemplary tissue targets may include liver, skeletal muscle, heart muscle, adipose deposits, kidney, lung, vascular endothelium, epithelial and/or hematopoietic cells. In a preferred embodiment, it is administered by intrahepatic injection, i.e. injection into the interstitial space of hepatic tissue.

The amount of product of the invention that is administered to the subject or patient may vary depending on the particular circumstances of the individual subject or patient including, age, sex, and weight of the individual; the nature and stage of the disease, the aggressiveness of the disease; the route of administration; and/or concomitant medication that has been prescribed to the subject or patient. Dosage regimens may be adjusted to provide the optimum therapeutic response.

For any particular subject, specific dosage regimens may be adjusted over time according to the individual needs and the professional judgment of the person administering or supervising the administration of the compositions. Dosage ranges set forth herein are exemplary only and do not limit the dosage ranges that may be selected by medical practitioners.

In one embodiment, an AAV viral particle according to the invention can be administered to the subject or patient for the treatment of PFIC2 disease in an amount or dose comprised within a range of $5\times10^{11}$ to $1\times10^{15}$ vg/kg (vg: viral genomes; kg: subject's or patient's body weight). In a more particular embodiment, the AAV viral particle is administered in an amount comprised within a range of $1\times10^{13}$ to $1\times10^{14}$ vg/kg. In a more particular embodiment, the AAV viral particle is administered at a dosage of at least $2\times10^{13}$ vg/kg, preferably $3.5\times10^{13}$ vg/kg, more preferably $5\times10^{13}$ vg/kg, and more preferably $6\times10^{3}$ vg/kg.

Kit

In another aspect, the invention further relates to a kit comprising a nucleic acid construct, expression vector, host cell, viral particle or pharmaceutical composition of the invention in one or more containers. The kit may include instructions or packaging materials that describe how to administer the nucleic acid construct, expression vector, viral particle, host cell or pharmaceutical compositions contained within the kit to a patient. Containers of the kit can be of any suitable material, e.g., glass, plastic, metal, etc., and of any suitable size, shape, or configuration. In certain embodiments, the kits may include one or more ampoules or syringes that contain the products of the invention in a suitable liquid or solution form.

The following examples are provided by way of illustration, and they are not intended to be limiting of the present invention. Furthermore, the present invention covers all possible combinations of particular and preferred embodiments described herein.

EXAMPLES

Molecular Engineering of Plasmid Containing the AAV Vectors Genome Bearing the Human ABCB11 cDNA Downstream of the Alpha-1 Antitrypsin (A1AT) Promoter.

The human ATP binding cassette subfamily B member 11 (ABCB11) gene, also called bile salt export pump (hBSEP) gene, cDNA sequence (3,963 bp) was used to generate two plasmids allowing further AAV particle production bearing either the wild-type hBSEP cDNA or a codon optimized version of it. For both plasmids, the cDNA sequence was cloned downstream of the A1AT promoter, and this expression cassette was further inserted into an AAV2 DNA backbone using a pAAV2 plasmid (Agilent Technologies, Santa Clara, CA).

For generating the co-hBSEP bearing plasmid, a synthetic DNA cassette was generated (GeneScript, Piscataway, NJ) containing the A1AT promoter upstream a codon-optimized hBSEP cDNA sequence based on the human ABCB11 protein (NCBI Reference Sequence: NP_003733.2). This cassette was then inserted between the two internal terminal repeats (ITR) of an AAV2 plasmid backbone (pAAV2), generating the pAAV-co-hBSEP. The resulting AAV-co-hBSEP vector genome has a size of 4,734 b, which is within the packaging limits of AAV particles. The pAAV-co-hBSEP was controlled by sequencing and restriction enzyme analysis. This plasmid allows for the generation of the AAV-co-hBSEP vector of any serotype or capsid variant.

The wild-type hBSEP (wt-hBSEP) cDNA bearing plasmid was generated by substituting in pAAV-co-hBSEP the Sal I-Nde I fragment (4,004 bp) containing the co-hBSEP cDNA by a sequence of identical length containing the wt-hBSEP cDNA (NCBI Reference Sequence: NM_003742.4). This last sequence was also synthetized (GeneScript) and cloned into the pAAV2 plasmid. This cloning presented difficulties and could only be achieved by growing bacterial colonies at 30° C. instead of 37° C., since this last temperature resulted in undesired plasmid rearrangements. The resulting pAAV-wt-hBSEP plasmid containing AAV-wt-hBSEP vector sequence (4,734 pb) was verified by sequencing and restriction analysis. This plasmid allows for the generation of the AAV-wt-hBSEP vector of any serotype or capsid variant.

The diagram showing the two AAVAnc80 vectors (of the same length) is presented FIG. 1.

Analysis of BSEP Expression in Human Hepatic Cells

Figure 2:
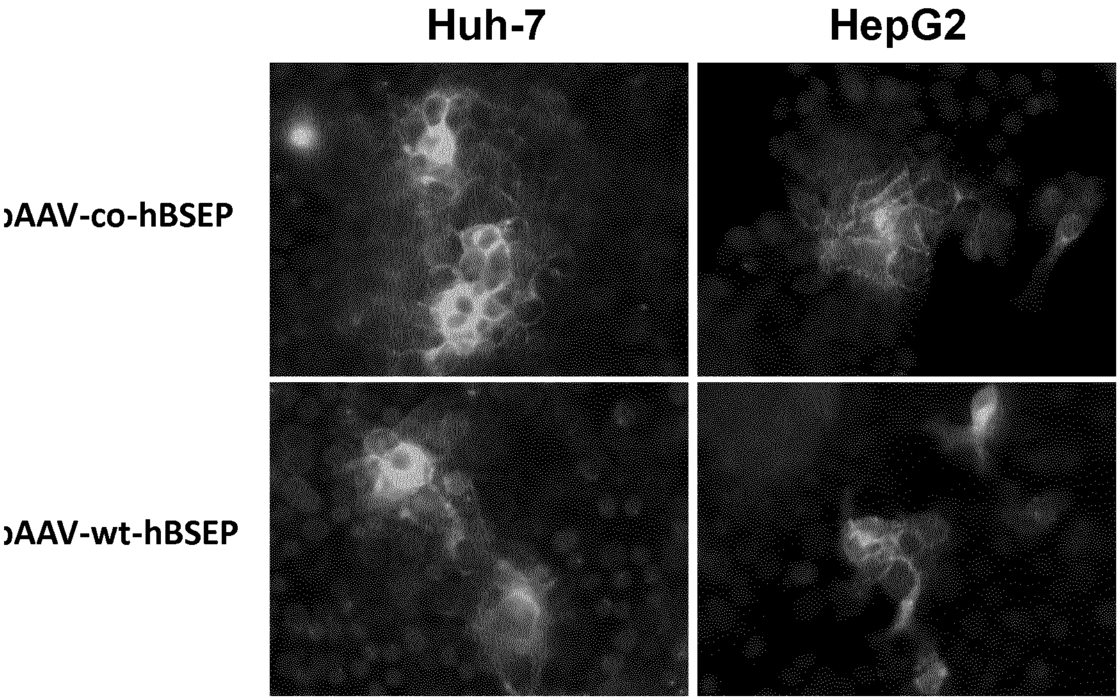

Huh-7 and HepG2 cells were transfected with the plasmids pAAV-co-hBSEP and pAAV-wt-hBSEP using lipofectamin 2000. Cells were fixed at 48-72 h and human BSEP was detected by immunofluorescence using a primary mouse antibody specific for BSEP (Santa Cruz sc-74500; working dilution 1:1500) (FIG. 2). A donkey anti-mouse IgG Alexa-488-conjugated secondary antibody (Invitrogene ref. A21202; working dilution 1:1,000) was used for detection. As show in FIG. 2, both plasmids can express specific hBSEP in both cell lines with most cells showing membrane localization of the protein.

Production of AAVAnc80 Viral Particles Containing ABCB11 cDNA Expressing hBSEP

The inventors produced AAV vectors based on the in silico designed AAV ancestral sequence Anc80 (Zinn, E., et al. Cell Reports, 2015; 12:1056-1068). To produce AAVAnc80 viral particles (VPs), thirty 150-$cm^2$-flasks containing confluent HEK293T cell monolayers were co-transfected with plasmids pδF6, pAnc80-AAP2, and the AAV plasmid containing the vector sequence to be packaged (AAV-co-hBSEP or AAV-wt-hBSEP) using polyethyenimine (PEI). After 72 h of incubation, AAV particles were purified from the supernatant and cells by ultracentrifugation using a iodixanol gradient as described (Murillo, O., et al. Journal of Hepatology, 2016; 64:419-426). Finally, the purified virus was concentrated using Amicon Ultra Centrifugal Filters-Ultracel 100K (Millipore) and titrated by qPCR using oligonucleotides specific for the A1AT promoter (Forward primer: 5'-TTGCTCCTCCGATAACTGGG-3' (SEQ ID NO: 9); Reverse primer: 5'-CCCTGTCCTCGTCCGTATTT-3'(SEQ ID NO: 10)).

Several batches were generated for each vector, which titers are indicated in Table 1. Unexpectedly, AAVAnc80-wt-hBSEP was very difficult to produce, with only one out of six stocks generated having a sufficient titer compatible with in vivo application (above $5\times10^{11}$ vg/mL). On the opposite, twelve batches of AAVAnc80-co-hBSEP out of 14 were produced within the expected yield and titer, only two batches showing titers bellow $5\times10^{11}$ vg/mL.

TABLE 1

Titers of AAVAnc80-hBSEP viral stocks*

| Stock number | AAVAnc80-co-hBSEP (vg/mL) | AAVAnc80-wt-hBSEP (vg/mL) |
|---|---|---|
| 1 | $2.81 \times 10^{12}$ | $4.89 \times 10^{12}$ |
| 2 | $6.80 \times 10^{11}$ | $\mathbf{2.60 \times 10^{11}}$ |
| 3 | $3.29 \times 10^{12}$ | $\mathbf{0.74 \times 10^{10}}$ |
| 4 | $8.82 \times 10^{12}$ | $\mathbf{5.42 \times 10^{10}}$ |
| 5 | $1.18 \times 10^{12}$ | $\mathbf{7.95 \times 10^{10}}$ |
| 6 | $\mathbf{2.70 \times 10^{11}}$ | |
| 7 | $\mathbf{4.70 \times 10^{11}}$ | |
| 8 | $1.45 \times 10^{12}$ | |
| 9 | $6.80 \times 10^{11}$ | |
| 10 | $6.19 \times 10^{12}$ | |
| 11 | $3.34 \times 10^{12}$ | |
| 12 | $2.04 \times 10^{12}$ | |
| 13 | $5.85 \times 10^{12}$ | |
| 14 | $2.94 \times 10^{12}$ | |
| Mean | $2.86 \times 10^{12}$ | $1.07 \times 10^{12}$ |
| SD[a] | $2.53 \times 10^{12}$ | $2.13 \times 10^{12}$ |

Figure 3:
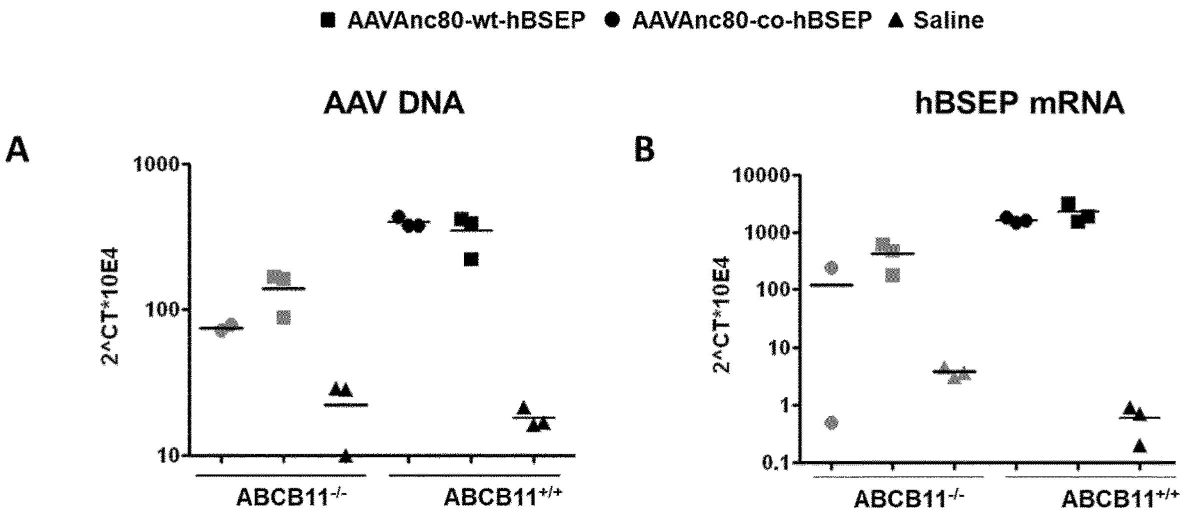
FIG. 3. AAVAnc80 liver transduction in Abcb11$^{-/-}$ and Abcb11$^{+/+}$ mice. Female mice having the indicated genotypes received $2\times10^{13}$ vg/kg of AAVAnc80-co-hBSEP, AAVAnc80-wt-hBSEP or an equivalent volume of saline. Mice were sacrificed one month later and AAV viral DNA (A) or hBSEP mRNA levels (B) were quantified in liver extracts by qPCR or RT-qPCR, respectively. ΔCt corresponds to Ct for house-keeping gene GAPDH—Ct for A1AT promoter sequence (A) or Ct for house-keeping gene GAPDH—Ct for human ABCB11 codon optimized or non-codon optimized gene (B).

*Stocks with a titer <$5 \times 10^{11}$ vg/ml (too low to be used in vivo) are indicated in bold Evaluation of BSEP Expression in Abcb11$^{-/-}$ Mice Injected with AAVAnc80 Particles In order to test the expression of hBSEP in vivo, the inventors used the C57BL/6 knock-out mouse model for Abcb11 gene (Abcb11$^{-/-}$ mice), which do not to express BSEP (Zhang, Y. Y., et al. Journal of Biological Chemistry, 2012, 287: 24784-24794). Four-week-old Abcb11$^{-/-}$ female mice were injected intravenously, using the retro-orbital route, with $2\times10^{13}$ vg/kg of AAVAnc80-wt-hBSEP (n=2), AAVAnc80-co-hBSEP (n=3), or with an equivalent volume of saline (n=3). Wild-type mice (Abcb11$^{+/+}$) were also inoculated with the same amount of vectors to compare the transduction efficacy of AAV vectors between Abcb11$^{-/-}$ and Abcb11$^{+/+}$ mice. One month later, mice were sacrificed and liver samples were obtained. Liver homogenates were used to determine the amount of viral genomes and hBSEP mRNA in each mouse by quantitative PCR (qPCR) and reverse transcription (RT)-qPCR, respectively. In the first case, DNA was extracted using the Nucleospin tissue purification kit (Macherey Nagel) following the manufacturer's instructions, and a qPCR was performed with oligonucleotides specific for the A1AT promoter sequence (see primer sequences in previous part). Although both AAV vectors showed a similar level of AAV DNA in Abcb11$^{+/+}$ mice, the AAVAnc80-wt-hBSEP vector had lower level of AAV DNA than AAVAnc80-co-hBSEP in Abcb11$^{-/-}$ mice (FIG. 3A). To determine the level of hBSEP mRNA expression, RNA was extracted from liver samples with the Maxwell® 16 LEV simplyRNA tissue kit (Promega), following the manufacturer's instructions. In this case, a RT reaction was first performed with random primers followed by a qPCR with primers specific for either codon optimized or wild type ABCB11 genes (for wt-hBSEP: 5'-TCATCCGAAATCCCAAGATT-3'(SEQ ID NO: 11) and 5'-CAAGCGATGAGCAACTGAA-3' (SEQ ID NO: 12); for co-hBSEP 5'-TAATTTCCAGGGCAAGATCG-3' (SEQ ID NO: 13) and 5'-AGCAGCTGGATAGAGGTGGA-3' (SEQ ID NO: 14). Although the results for both vectors cannot be directly compared due to the difference in the set of primers used to specifically amplify each of the two vectors, mRNA levels were 5 to 10 fold higher in Abcb11$^{++}$ mice compared to Abcb11$^{-/-}$ mice for each vector (FIG. 3B). In both cases, the primers that were used did not detect murine Abcb11 mRNA, as shown by the very low signal obtained in mice that did not receive AAV vectors.

Figure 4:
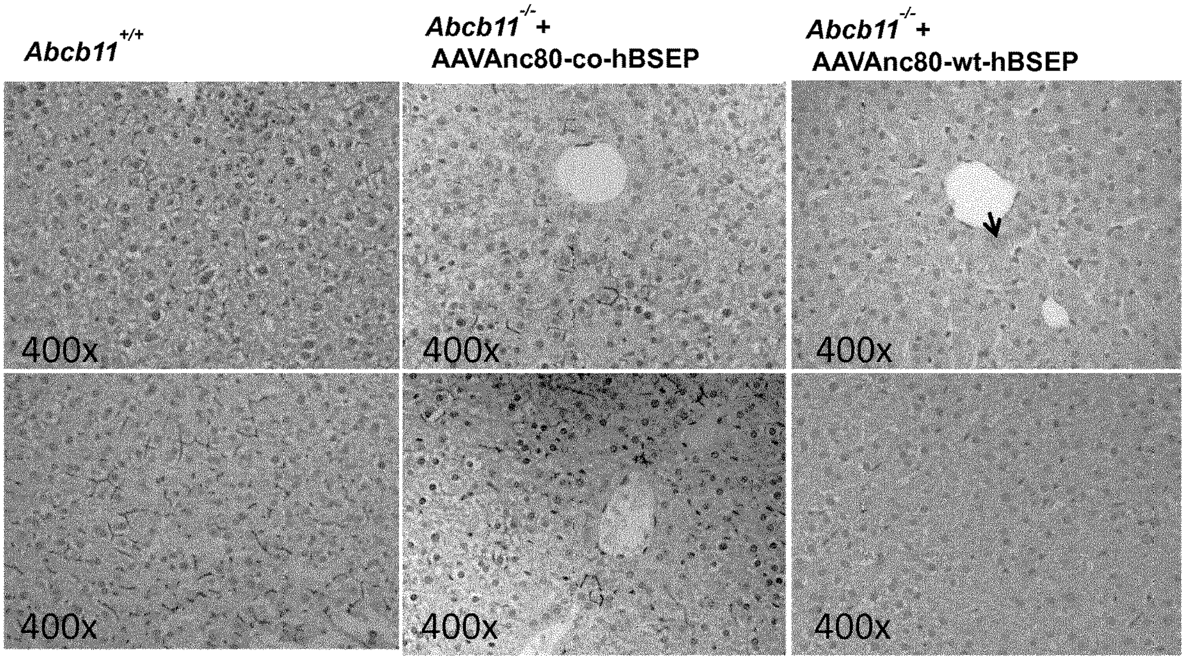
FIG. 4. hBSEP expression in vivo. Four-week-old female Abcb11$^{-/-}$ mice received $2\times10^{13}$ vg/mL of AAVAnc80-co-hBSEP or AAVAnc80-wt-hBSEP and expression was analyzed one month later by immunohistochemistry. Female Abcb11$^{+/+}$ mice were used as positive control for hBSEP staining (left panel). Female Abcb11$^{-/-}$ mice receiving AAVAnc80-co-hBSEP are in the middle panel. The arrow indicates one of the very few hBSEP positive cells detected in mice receiving AAVAnc80-wt-hBSEP (right panel). Representative pictures from two mice in each group are shown.

Finally, hBSEP expression was analyzed in liver samples by immunohistochemistry using a BSEP specific antibody conjugated with horseradish peroxidase (Santa Cruz sc-74500). This analysis showed a strong hBSEP expression in Abcb11$^{-/-}$ mice that had received the AAVAnc80-co-hBSEP vector, in which a clear canaliculi staining was observed, similar to Abcb11$^{+/+}$ mice used as control (FIG. 4, left and middle panels). In contrast, and unexpectedly, Abcb11$^{-/-}$ mice that were inoculated with AAVAnc80-wt-hBSEP showed very few cells expressing BSEP, which in addition had a very weak staining (FIG. 4, right panel), indicating that this cDNA sequence is not efficiently suitable for hBSEP expression in vivo.

Therapeutic Efficacy of AAVAnc80-Co-hBSEP in Abcb11$^{-/-}$ Mice

For this experiment, the inventors used Abcb11$^{-/-}$ mice, which reproduce most of PFIC2 symptoms observed in patients, having a more severe phenotype in females compared to males. These mice show elevation of transaminases (ALT and AST), alkalyne phosphatase (ALP, a cholestasis marker), bilirubin, and develop liver fibrosis (Zhang, Y. Y., et al. Journal of Biological Chemistry, 2012, 287: 24784-

Figure 5:
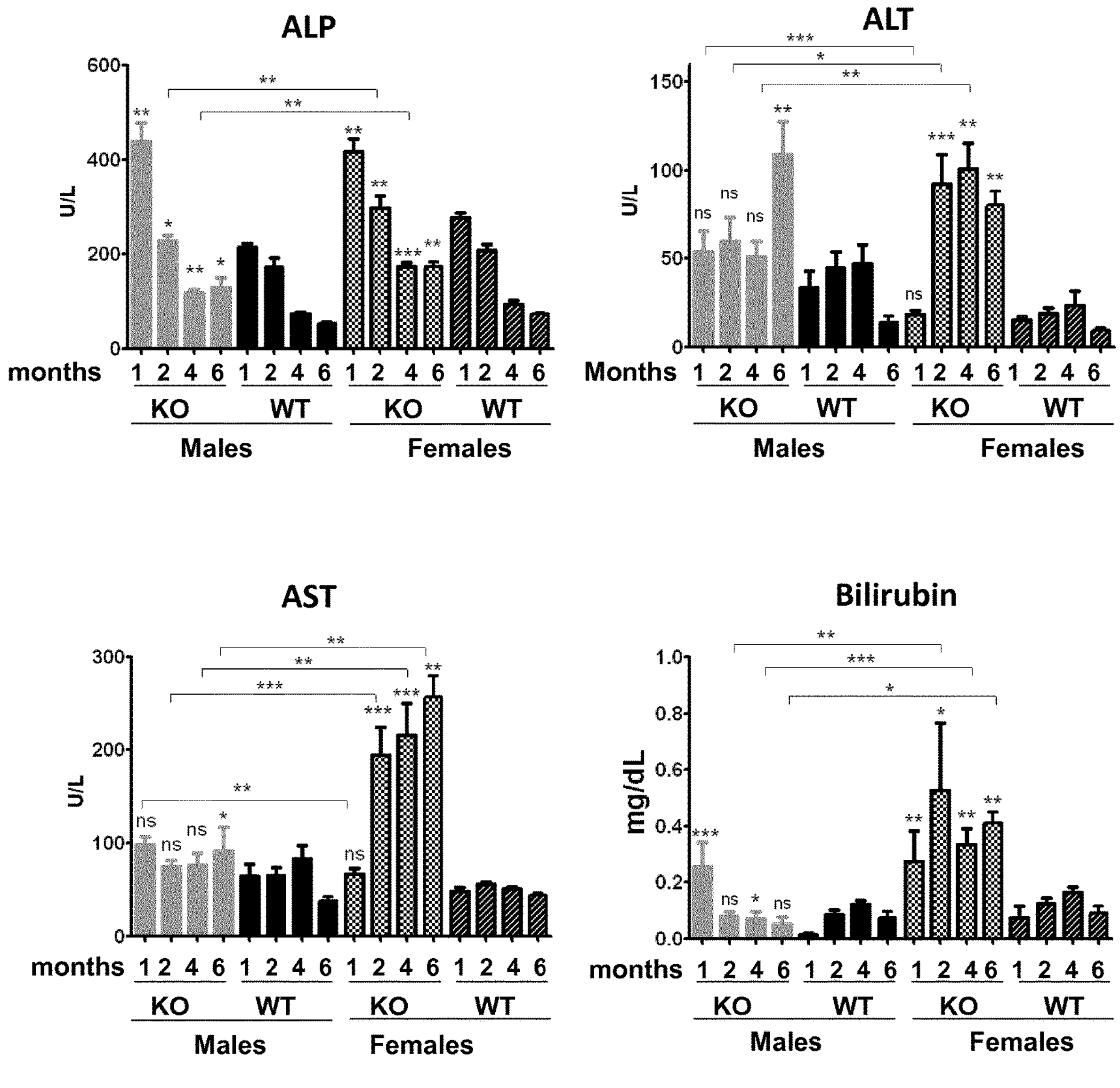
FIG. 5. Serum markers in Abcb11$^{-/-}$ and Abcb11$^{+/+}$ mice. ALP, ALT, AST, and bilirubin serum biomarkers were analyzed in the serum of Abcb11$^{-/-}$ (KO) and Abcb11$^{+/+}$ (WT) mice (n>5 in all groups) at the indicated age (months) using a COBAS analyzer (Roche). The statistical analysis was performed using a ManWhitney test (signs above KO bars show comparison with WT mice of the same age and gender; horizontal bars show comparisons between male and female KO of the same age). *, $p<0.05$; , $p<0.01$; *, $p<0.001$; ns, not significant; U/L, units/L FIG. 6. ALP, transaminase, and bilirubin levels in Abcb11$^{-/-}$ mice after AAVAnc80-co-hBSEP treatment. Four-week old Abcb11$^{-/-}$ mice were treated with $6\times10^{3}$ vg/kg of AAVAnc80-co-hBSEP (+BSEP) or left untreated (nt) and the levels of ALP, ALT, AST, and bilirubin were determined in serum at the indicated mice ages (n>7 in all groups). Empty bars correspond to basal levels in treated mice. The statistical analysis was performed using a Man-Whitney test. *, $p<0.05$; **, $p<0.01$; ns, non-significant.
Figure 7:
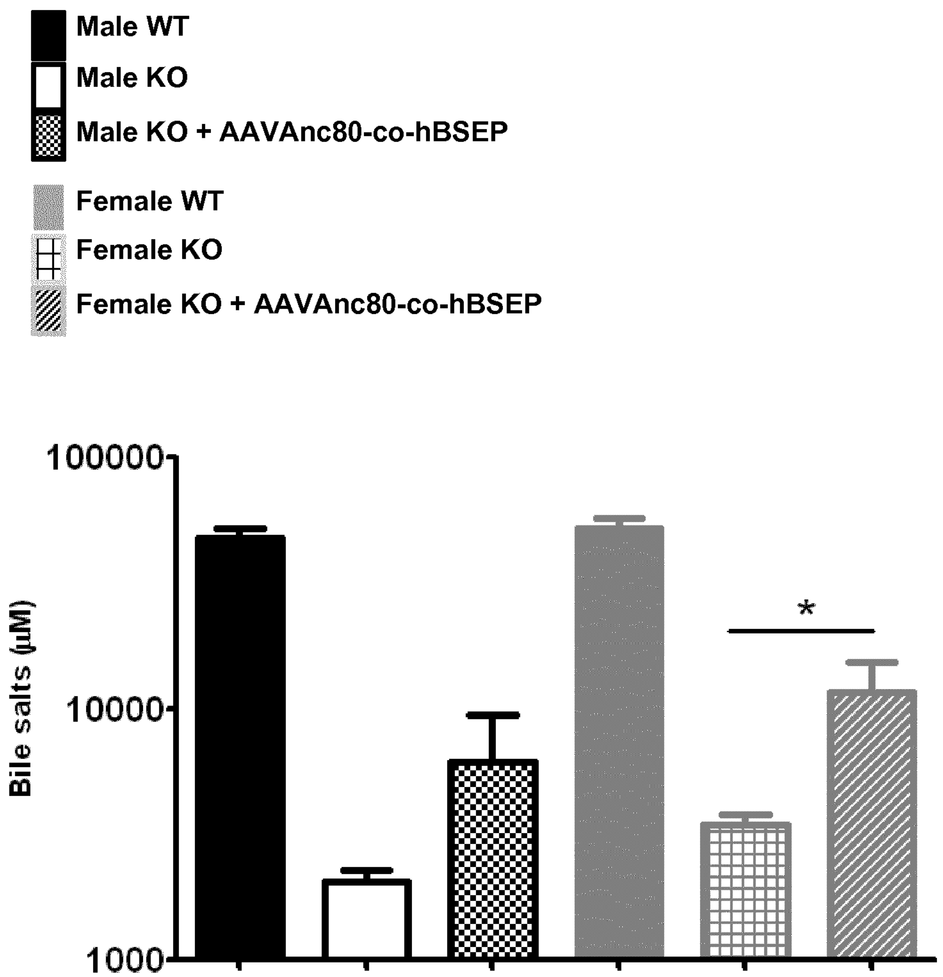
FIG. 7. Biliary bile salt levels in Abcb11$^{-/-}$ mice one month after AAVAnc80-co-hBSEP treatment. Four-week old Abcb11$^{-/-}$ mice (n=3 or 4) were treated with $6\times10^{13}$ vg/kg or left untreated and one month later mice were sacrificed and the level of bile salts in bile were determined with a COBAS analyzer (Roche) and compared to Abcb11$^{+/+}$ mice of the same age. The statistical analysis was performed using a ManWhitney test. *, $p<0.05$.

24794) (FIG. 5). These symptoms develop after two months of age in females but take up to six months to appear in male animals. In contrast to patients, bile salts are not elevated in $Abcb11^{-/-}$ mice (data not shown). In addition, both male and female $Abcb11^{-/-}$ mice show a dramatic decrease of biliary bile salts as early as one month of age (FIG. 7).

Figure 6:
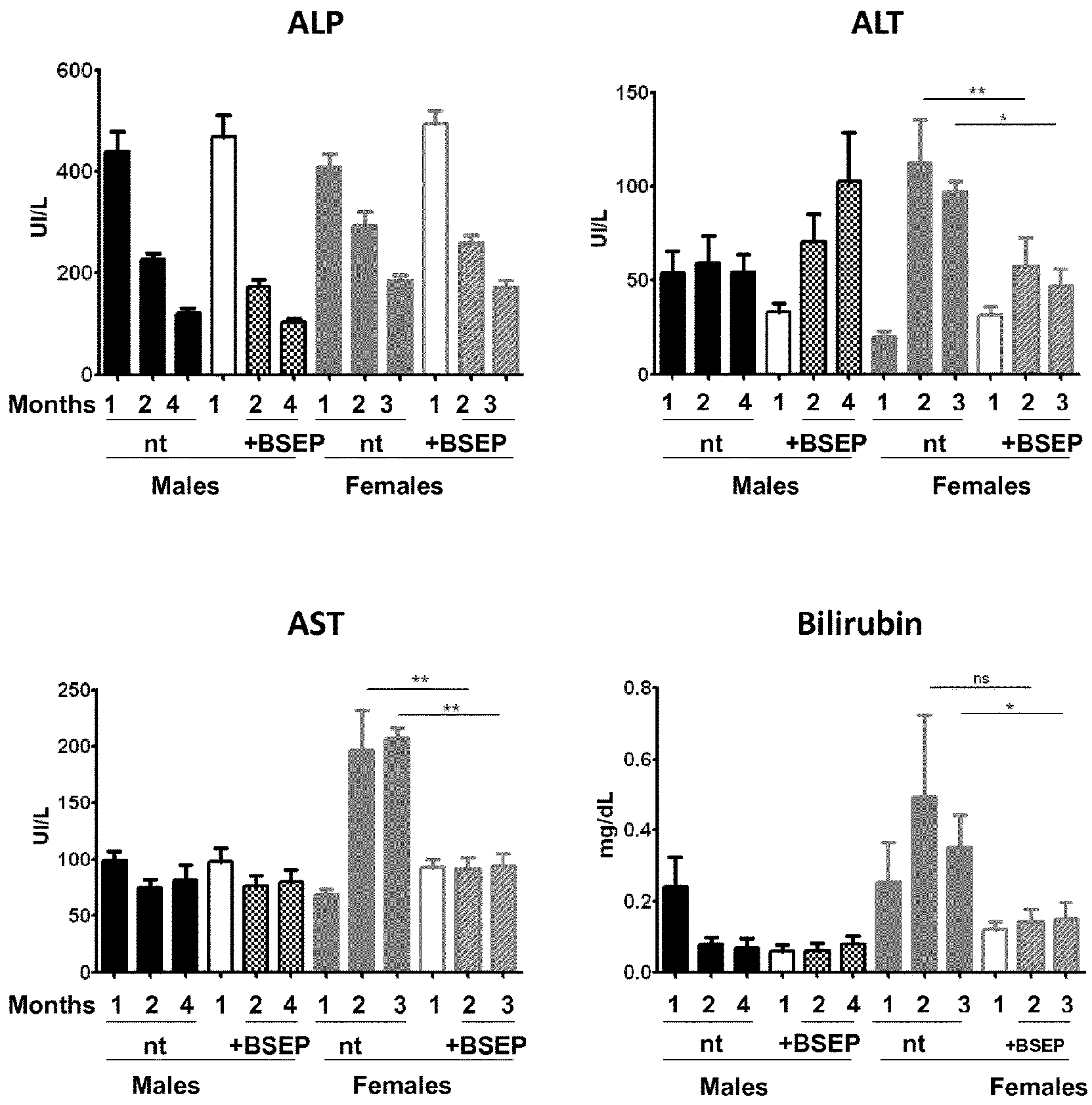

Four week old $Abcb11^{-/-}$ female and male mice were injected intravenously, using the retro-orbital route, with $6\times10^{13}$ vg/kg AAVAnc80-co-hBSEP. Non-treated mice were used as controls. Mice were bled at 1, 2, and 3 or 4 months after treatment and the following parameters were measured in serum: ALP, ALT and AST, bile salts, cholesterol, and bilirubin. No significant changes were observed in bile salts and cholesterol, as expected for this model (data not shown). Female $Abcb11^{-/-}$ mice that received AAVAnc80-co-hBSEP showed a significant decrease in ALT and AST at one and two months after treatment, and of bilirubin at two months post-treatment (FIG. 6). In the case of male $Abcb11^{-/-}$-treated mice, transaminase and bilirubin levels were similar to those of non-treated mice, but at this age these markers are within the normal range in healthy mice (mean for $Abcb11^{+/+}$ mice: ALT=47.5 U/L; AST=83.25 U/L; bilirubin: 0.08 mg/dL). ALP levels diminished with age in all mice, but the reduction observed in treated females two months after treatment was higher (3 fold) compared to non-treated females (2.2 fold). It is important to notice that ALP levels in $Abcb11^{-/-}$ mice are only slightly elevated compared to $Abcb11^{+/+}$ mice (FIG. 5). Finally, treated $Abcb11^{-/-}$ mice significantly increased biliary bile salt levels one month after treatment (FIG. 7), partially restoring the secretion of bile salts to bile, which is the main biomarker of PFIC2 patients, indicating a physiologic rescue of BSEP activity.

Figure 8:
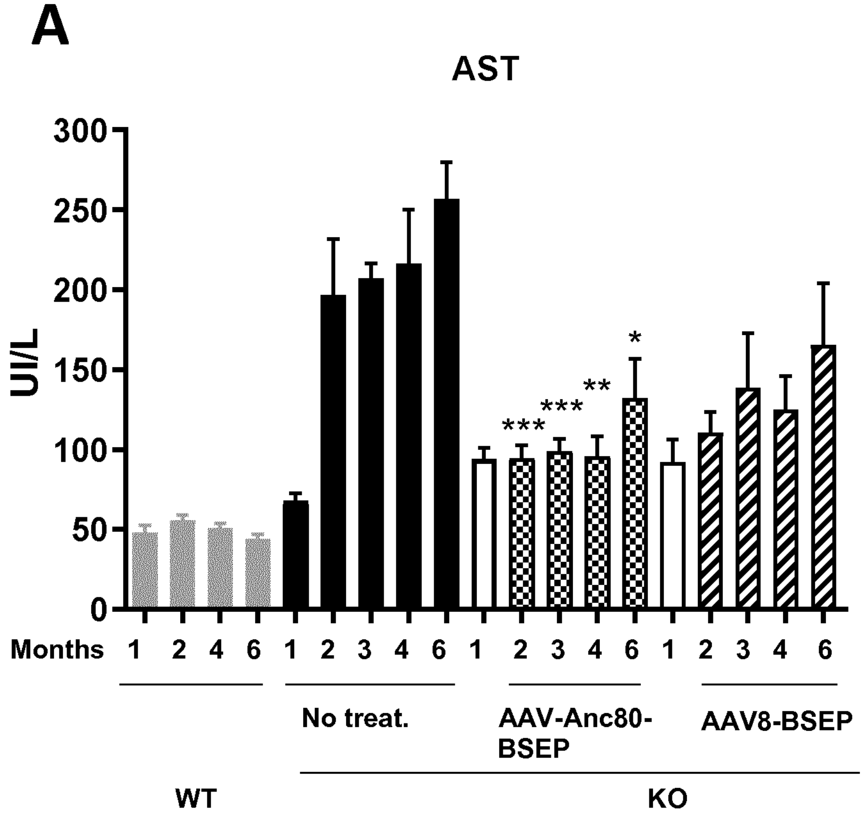
FIG. 8. Serum markers in Abcb11$^{-/-}$ mice treated with AAV vectors expressing BSEP. Four-week old Abcb11$^{-/-}$ mice (KO) were treated with $6\times10^{13}$ vg/kg of AAVAnc80-co-hBSEP (AAVAnc80-BSEP), AAV8-co-hBSEP (AAV8-BSEP) or left untreated (No treat.). Levels of AST (A) and bilirubin (B) were determined in serum at the indicated ages (months, n>4 in all groups) using a COBAS analyzer (Roche). Non-treated Abcb11$^{+/+}$ mice (WT) were used as controls. Empty bars correspond to basal levels in treated mice. Statistical analysis was performed comparing treated and non-treated KO mice of the same age using a ManWhitney test. *, $p<0.05$; , $p<0.01$; *, $p<0.001$. U/L, units/L.
Figure 8:
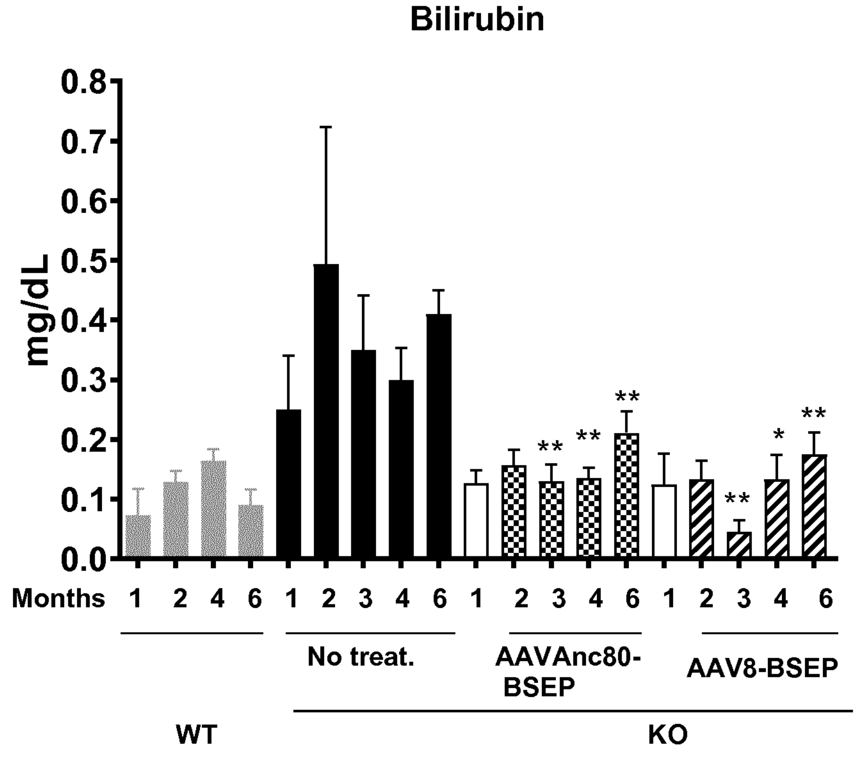
Figure 9:
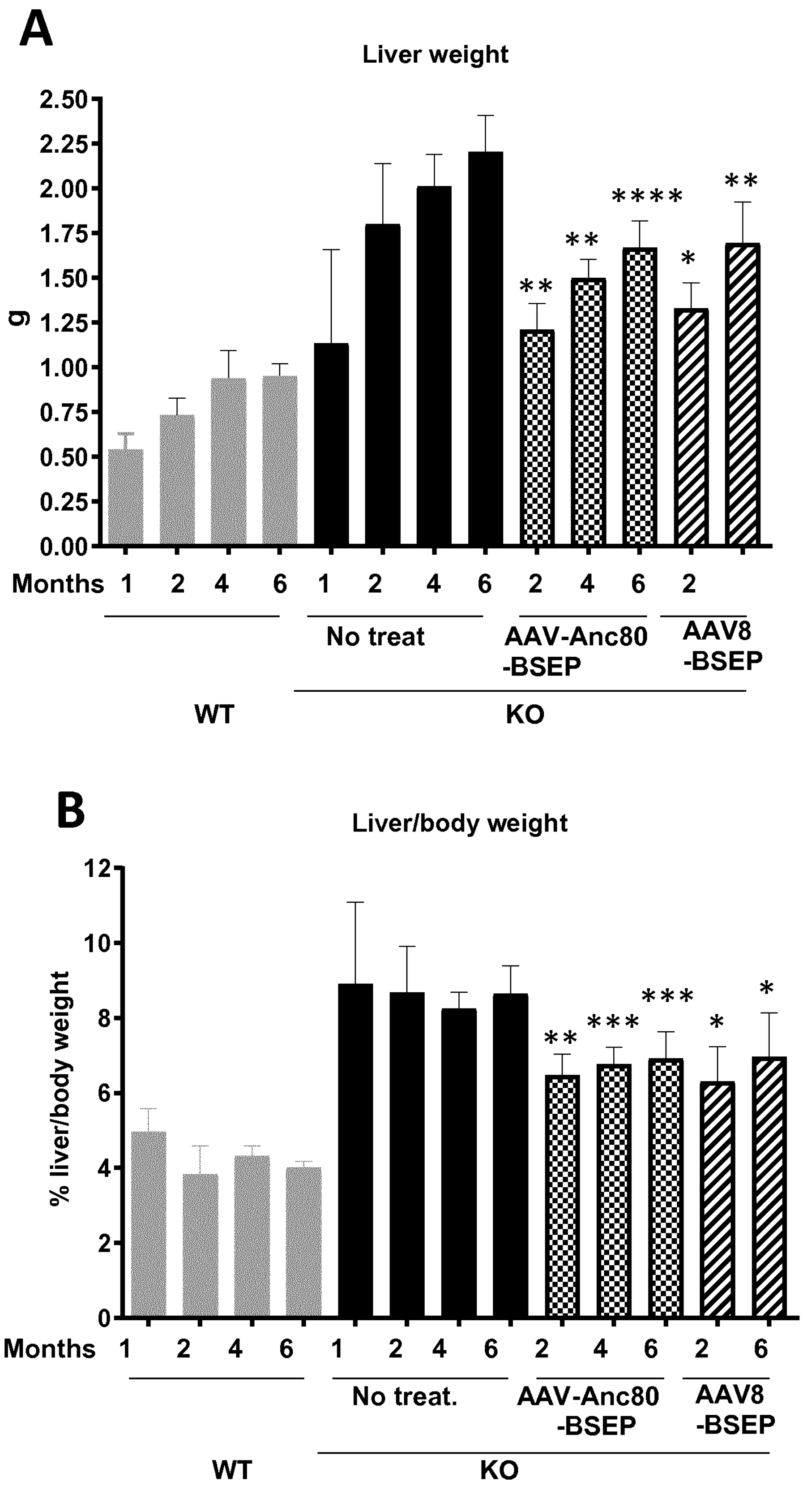
FIG. 9. Liver weight in Abcb11$^{-/-}$ mice treated with AAV vectors expressing BSEP. Four-week old Abcb11$^{-/-}$ mice (KO) were treated with AAVAnc80-co-hBSEP and AAV8-co-hBSEP as described in FIG. 8. Liver weight (A) and the ratio of liver/body weight (B) were determined at the indicated ages (months). Non-treated Abcb11$^{+/+}$ mice (WT) were used as controls. Statistical analysis was performed comparing treated and non-treated KO mice of the same age using a ManWhitney test. *, $p<0.05$; , $p<0.01$; *, $p<0.001$, ****, $p<0.0001$.
Figure 10:
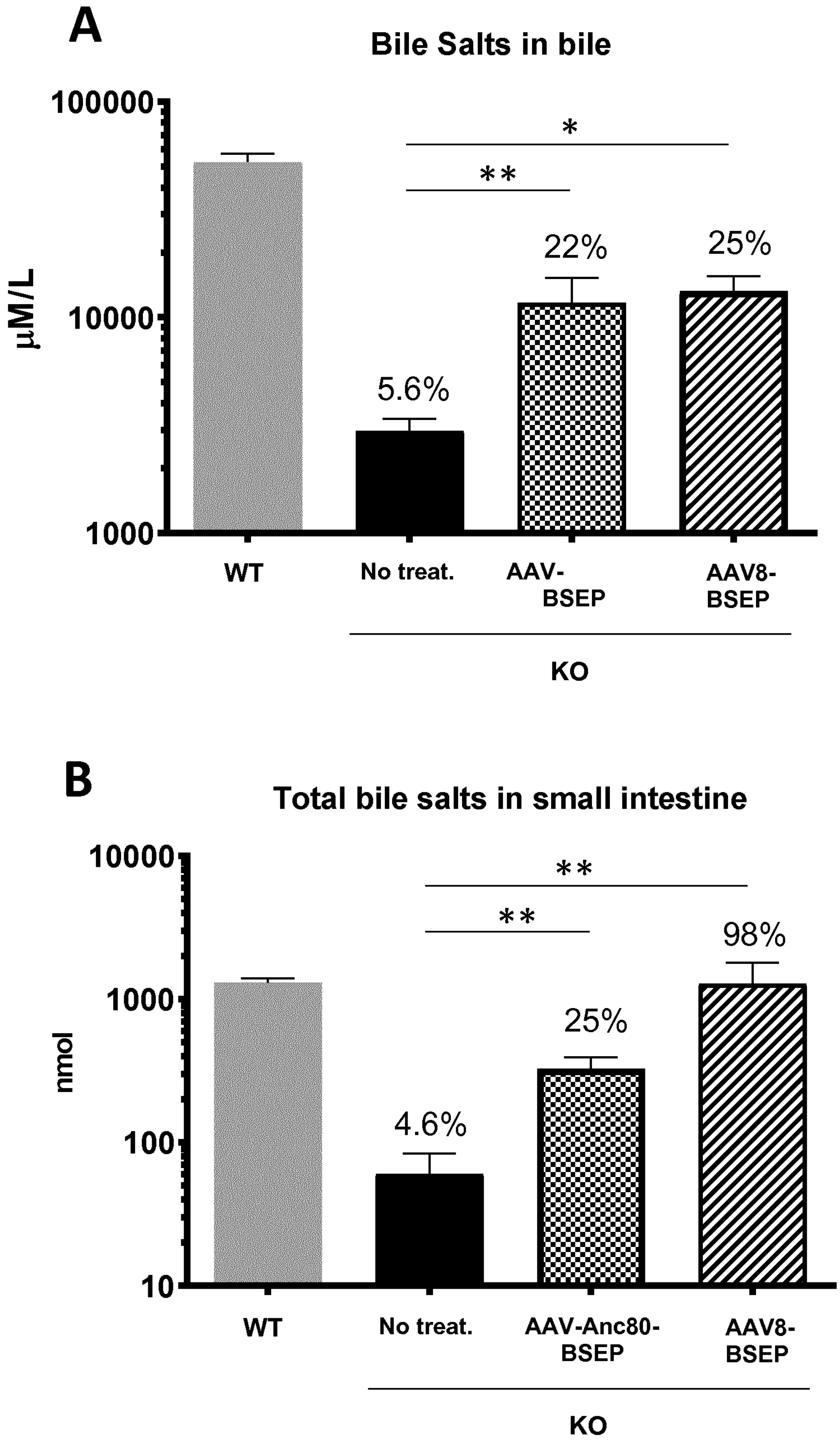
FIG. 10. Secretion of bile salts in Abcb11$^{-/-}$ mice treated with AAV vectors expressing BSEP. Four-week old Abcb11$^{-/-}$ mice (KO) were treated with AAVAnc80-co-hBSEP and AAV8-co-hBSEP as described in FIG. 8. Mice were sacrificed at two months of age and bile salt levels were determined in bile (A) and small intestine (B) with a COBAS analyzer (Roche). Numbers above the bars indicate the percentage of bile salts related to levels present in Abcb11$^{+/+}$ mice (WT). The statistical analysis was performed using a ManWhitney test. *, $p<0.05$, **$p<0.01$.

Long-Term Follow-Up of $Abcb11^{-/-}$ Female Mice Treated with AAVAnc80-Co-hBSEP In this study, the inventors used $Abcb11^{-/-}$ female mice, since only mice of this gender reproduce PFIC2 symptoms observed in patients (see FIG. 5). Four-week old $Abcb11^{-/-}$ female mice were injected intravenously, using the retro-orbital route, with $6\times10^{13}$ viral genomes (vg)/kg of AAVAnc80-co-hBSEP. Mice were sacrificed at one (n=6), three (n=6), and five (n=10) months after treatment. Mice were also bled at 1, 2, 3, and 5 months after treatment (mice sacrificed at one and three months after treatment were only bled until these time points). Non-treated $Abcb11^{-/-}$ and $Abcb11^{+/+}$ mice were used as negative and positive controls, respectively. $Abcb11^{-/-}$ mice that received AAVAnc80-co-hBSEP showed a significant reduction of serum biomarkers, like AST and bilirubin, up to five months post-treatment when compared with non-treated $Abcb11^{-/-}$ mice (FIG. 8A-B). In addition, treated $Abcb11^{-/-}$ mice also showed a significant reduction in liver weight and liver/body ratio compared to non-treated $Abcb11^{-/-}$ mice at all measured times (FIG. 9A-B). These data indicated that AAVAnc80-co-hBSEP-based therapy was able to control the progression of the disease in $Abcb11^{-/-}$ female mice. In order to determine whether the therapeutic effect was due to the restoration of bile salt secretion from hepatocytes to bile, the inventors measured the amount of bile salts in bile and small intestine of treated $Abcb11^{-/-}$ mice one month after treatment. As shown in FIG. 10, treatment with AAVAnc80-co-hBSEP was able to partially restore bile salt secretion in $Abcb11^{-/-}$ female mice, reaching levels that represented approximately 22% and 25% of bile salt levels found in the bile and small intestine of $Abcb11^{+/+}$ mice, respectively. In addition, bile salt levels found in treated $Abcb11^{-/-}$ mice were approximately 4 and 5.4 fold higher than those found in bile and intestine of non-treated $Abcb11^{-/-}$ mice, respectively.

AAV8-Co-hBSEP can Also Induce Therapeutic Effects in $Abcb11^{-/-}$ Female Mice

Once the inventors had shown that AAVAnc80-co-hBSEP could induce therapeutic effects in $Abcb11^{-/-}$ female mice, they evaluated whether these effects could also be achieved by using an AAV vector with serotype 8 expressing the same transgene (AAV8-co-hBSEP). Four-week old $Abcb11^{-/-}$ female mice were injected intravenously with $6\times10^{13}$ vg/kg of AAV8-co-hBSEP and bled periodically as described in the previous part. Mice were sacrificed at one (n=4) and five (n=6) months after treatment. Non-treated $Abcb11^{-/-}$ and $Abcb11^{+/+}$ mice were used as negative and positive controls, respectively. As in the case of AAVAnc80-co-hBSEP-treated mice, those that received AAV8-co-hBSEP showed a reduction of serum biomarkers, like AST and bilirubin, up to five months post-treatment compared with non-treated $Abcb11^{-/-}$ mice (FIG. 8A-B). In addition, a significant reduction in hepatomegaly was observed in AAV8-co-hBSEP-treated mice when compared with non-treated $Abcb11^{-/-}$ mice (FIG. 9A-B). Finally, treatment with AAV8-co-hBSEP was also able to partially restore bile salt secretion in $Abcb11^{-/-}$ female mice, reaching levels that represented approximately 25% and 98% of bile salt levels found in the bile and small intestine of $Abcb11^{+/+}$ mice, respectively (FIG. 10). In addition, bile salt levels found in treated $Abcb11^{-/-}$ mice were approximately 4.4 and 21 fold higher than those found in bile and intestine of non-treated $Abcb11^{-/-}$ mice, respectively.

CONCLUSIONS

From these results the inventors can conclude that liver delivery of a codon-optimized version of human BSEP gene from AAV vectors with either Anc80 or 8 serotypes results in a long-lasting therapeutic effect in a clinically relevant animal model of PFIC2 disease. Specifically, both AAVAnc80-co-hBSEP and AAV8-co-hBSEP vectors were able to partially restore bile salt secretion from the liver, resulting in control of transaminase and bilirubin levels, as well as of liver growth in treated mice.

Sequences for Use in Practicing the Invention

Sequences for use in practicing the invention are described below:

Codon-optimized sequence encoding BSEP (co-BSEP):

(SEQ ID NO: 1)

ATGAGCGACTCCGTGATTCTGAGATCAATCAAAAA

ATTCGGCGAAGAAAATGACGGGTTCGAGAGCGATA

AATCCTATAATAATGACAAGAAGTCTAGGCTGCAG

GACGAGAAGAAGGGCGATGGCGTGCGGGTGGGCTT

CTTTCAGCTGTTCCGGTTCAGCAGCAGCACCGACA

TCTGGCTGATGTTTGTGGGCAGCCTGTGCGCCTTC

CTGCACGGCATCGCACAGCCAGGCGTGCTGCTGAT

CTTTGGCACCATGACAGACGTGTTCATCGACTACG

ATGTGGAGCTGCAGGAGCTGCAGATCCCTGGCAAA

GCCTGCGTGAACAATACCATCGTGTGGACAAACAG

-continued

CTCCCTGAACCAGAATATGACCAACGGCACACGCT

GTGGCCTGCTGAATATCGAGTCTGAGATGATCAAG

TTTGCCAGCTACTATGCAGGAATCGCAGTGGCCGT

GCTGATCACCGGCTACATCCAGATTTGCTTCTGGG

TCATCGCAGCAGCAAGGCAGATCCAGAAGATGAGA

AAGTTCTATTTTCGGAGAATCATGCGGATGGAGAT

CGGCTGGTTTGACTGTAACTCTGTGGGCGAGCTGA

ATACAAGATTCAGCGACGACATCAACAAGATCAAT

GACGCCATCGCCGATCAGATGGCCCTGTTTATCCA

GCGGATGACCAGCACAATCTGTGGCTTCCTGCTGG

GCTTCTTTAGAGGCTGGAAGCTGACCCTGGTCATC

ATCAGCGTGTCCCCACTGATCGGAATCGGAGCAGC

AACAATCGGCCTGTCTGTGAGCAAGTTCACCGACT

ACGAGCTGAAAGCCTACGCCAAGGCAGGAGTGGTG

GCAGATGAAGTGATCAGCAGCATGAGGACCGTGGC

AGCCTTTGGCGGAGAGAAGAGGGAGGTGGAGCGGT

ACGAGAAGAACCTGGTGTTCGCCCAGCGGTGGGGC

ATCAGAAAGGGCATCGTGATGGGCTTCTTTACAGG

CTTCGTGTGGTGCCTGATCTTCCTGTGCTACGCCC

TGGCCTTTTGGTATGGCTCCACCCTGGTGCTGGAC

GAGGGAGAGTATACCCCTGGCACACTGGTGCAGAT

TTTCCTGAGCGTGATCGTGGGCGCCCTGAACCTGG

GAAATGCATCCCCATGCCTGGAAGCCTTCGCCACA

GGAAGGGCAGCAGCCACCTCCATCTTCGAGACAAT

CGACCGCAAGCCTATCATCGACTGTATGTCTGAGG

ATGGCTACAAGCTGGACAGGATCAAGGGCGAGATC

GAGTTTCACAATGTGACCTTCCACTATCCCAGCCG

CCCTGAGGTGAAGATCCTGAACGATCTGAATATGG

TCATCAAGCCAGGAGAGATGACCGCCCTGGTGGGA

CCCTCTGGAGCAGGCAAGAGCACCGCCCTGCAGCT

GATCCAGCGGTTTTACGACCCTTGCGAGGGAATGG

TGACCGTGGACGGACACGACATCAGGTCCCTGAAC

ATCCAGTGGCTGCGCGATCAGATCGGCATCGTGGA

GCAGGAGCCAGTGCTGTTCTCTACCACAATCGCCG

AGAATATCAGATACGGCCGCGAGGATGCCACAATG

GAGGACATCGTGCAGGCCGCCAAGGAGGCCAACGC

CTATAACTTCATCATGGATCTGCCCCAGCAGTTCG

ACACCCTGGTGGGAGAGGGAGGAGGACAGATGTCC

GGAGGCCAGAAGCAGAGAGTGGCCATCGCCAGAGC

CCTGATCCGCAACCCTAAGATCCTGCTGCTGGATA

-continued

TGGCCACAAGCGCCCTGGACAATGAGTCCGAGGCT

ATGGTGCAGGAGGTGCTGAGCAAGATCCAGCACGG

CCACACCATCATCTCTGTGGCACACAGGCTGAGCA

CAGTGAGAGCAGCCGACACCATCATCGGCTTTGAG

CACGGCACAGCAGTGGAGAGGGGCACCCACGAGGA

GCTGCTGGAGAGGAAGGGCGTGTACTTCACCCTGG

TGACACTGCAGTCCCAGGGCAACCAGGCCCTGAAT

GAGGAGGACATCAAGGATGCCACAGAGGACGATAT

GCTGGCCCGGACCTTCAGCAGAGGCTCCTATCAGG

ATTCTCTGAGGGCCAGCATCAGGCAGCGGAGCAAG

TCTCAGCTGAGCTACCTGGTGCACGAGCCACCTCT

GGCAGTGGTGGACCACAAGTCCACCTATGAGGAGG

ATCGCAAGGACAAGGACATCCCAGTGCAGGAGGAG

GTGGAGCCTGCACCAGTGAGGCGCATCCTGAAGTT

TTCCGCCCCAGAGTGGCCCTACATGCTGGTGGGAT

CTGTGGGAGCAGCAGTGAACGGCACCGTGACACCA

CTGTATGCCTTCCTGTTTTCCCAGATCCTGGGCAC

CTTCTCTATCCCCGACAAGGAGGAGCAGCGGTCCC

AGATCAATGGCGTGTGCCTGCTGTTTGTGGCTATG

GGCTGCGTGAGCCTGTTTACACAGTTCCTGCAGGG

CTACGCCTTCGCCAAGAGCGGCGAGCTGCTGACCA

AGCGGCTGAGAAAGTTCGGCTTTAGAGCCATGCTG

GGCCAGGACATCGCCTGGTTTGACGATCTGCGGAA

CAGCCCAGGCGCCCTGACCACAAGACTGGCCACAG

ATGCATCTCAGGTGCAGGGAGCAGCAGGCAGCCAG

ATCGGCATGATCGTGAACTCCTTCACCAATGTGAC

AGTGGCCATGATCATCGCCTTCAGCTTTTCCTGGA

AGCTGAGCCTGGTCATCCTGTGCTTCTTCCCCTTT

CTGGCCCTGAGCGGAGCAACCCAGACAAGGATGCT

GACCGGCTTCGCCTCCAGAGACAAGCAGGCCCTGG

AGATGGTGGGCCAGATCACAAACGAGGCCCTGAGC

AATATCAGGACCGTGGCAGGAATCGGCAAGGAGCG

GCGGTTCATCGAGGCCCTGGAGACAGAGCTGGAGA

AGCCTTTCAAGACCGCCATCCAGAAGGCCAACATC

TACGGCTTCTGCTTTGCCTTCGCCCAGTGTATCAT

GTTCATCGCCAACTCTGCCAGCTACCGCTATGGCG

GCTACCTGATCAGCAATGAGGGCCTGCACTTCAGC

TACGTGTTCAGAGTGATCAGCGCCGTGGTGCTGTC

TGCCACAGCCCTGGGAAGGGCCTTCTCCTACACCC

CATCTTATGCCAAGGCCAAGATCAGCGCCGCCAGG

TTCTTTCAGCTGCTGGACCGCCAGCCACCCATCAG

-continued

CGTGTACAACACAGCCGGCGAGAAGTGGGATAATT

TCCAGGGCAAGATCGACTTTGTGGATTGCAAGTTC

ACCTATCCTAGCAGACCAGACTCCCAGGTGCTGAA

TGGCCTGTCCGTGTCTATCAGCCCAGGCCAGACAC

TGGCCTTTGTGGGCTCCTCTGGCTGTGGCAAGTCC

ACCTCTATCCAGCTGCTGGAGCGGTTCTATGACCC

CGATCAGGGCAAAGTGATGATCGACGGCCACGATA

GCAAGAAGGTGAACGTGCAGTTTCTGAGATCCAAT

ATCGGCATCGTGTCTCAGGAGCCTGTGCTGTTCGC

CTGCTCCATCATGGATAACATCAAGTACGGCGACA

ATACAAAGGAGATCCCAATGGAGAGAGTGATCGCA

GCAGCAAAGCAGGCACAGCTGCACGATTTCGTGAT

GTCCCTGCCCGAGAAGTATGAGACAAACGTGGGCT

CTCAGGGCAGCCAGCTGTCCAGGGGCGAGAAGCAG

AGGATCGCAATCGCCAGGGCCATCGTGCGCGATCC

CAAGATCCTGCTGCTGGACGAGGCCACCAGCGCCC

TGGATACAGAGTCCGAGAAGACCGTGCAGGTGGCC

CTGGACAAGGCCCGGGAGGGAAGAACATGTATCGT

GATCGCCCACAGACTGAGCACCATCCAGAATGCCG

ACATCATCGCCGTGATGGCCCAGGGCGTGGTCATC

GAGAAGGGCACCCACGAGGAACTGATGGCACAGAA

AGGGGCTTACTACAAACTGGTCACAACAGGCTCAC

CTATCTCATAG

Codon-optimized sequence encoding BSEP #2 (co-BSEP-2)

(SEQ ID NO: 2)

ATGTCTGATTCTGTGATCCTGAGATCCATCAAGAA

ATTTGGGGAAGAGAATGATGGCTTTGAGTCTGACA

AGAGCTACAACAATGACAAGAAAAGCAGGCTGCAG

GATGAGAAAAAGGGTGATGGTGTCAGAGTGGGCTT

CTTCCAGCTGTTCAGATTCAGCAGCAGCACAGACA

TCTGGCTGATGTTTGTGGGCAGCCTGTGTGCCTTC

CTGCATGGAATTGCTCAGCCTGGGGTGCTGCTGAT

CTTTGGCACCATGACAGATGTGTTCATTGACTATG

ATGTGGAACTGCAAGAGCTGCAGATCCCTGGCAAG

GCTTGTGTGAACAACACCATTGTGTGGACCAACAG

CAGCCTGAACCAGAACATGACCAATGGCACCAGAT

GTGGCCTGCTGAACATAGAGTCTGAGATGATCAAG

TTTGCCAGCTACTATGCTGGCATTGCTGTGGCAGT

GCTGATCACAGGCTACATCCAGATCTGCTTTTGGG

TCATAGCTGCTGCCAGACAGATCCAGAAGATGAGG

AAGTTCTACTTTAGAAGGATCATGAGGATGGAAAT

-continued

TGGATGGTTTGACTGCAACTCTGTGGGAGAGCTGA

ACACCAGATTCTCTGATGACATCAACAAGATCAAT

GATGCCATTGCTGACCAGATGGCCCTGTTCATCCA

GAGGATGACCAGCACCATCTGTGGCTTTCTGCTGG

GCTTTTTCAGAGGCTGGAAGCTGACCCTGGTTATC

ATCTCTGTGTCCCCACTGATTGGCATTGGAGCTGC

CACCATTGGCCTGTCTGTGTCCAAGTTCACAGACT

ATGAGCTGAAAGCCTATGCCAAGGCTGGTGTTGTG

GCTGATGAAGTGATCAGCTCCATGAGAACAGTGGC

TGCCTTTGGTGGTGAAAAGAGGGAAGTTGAGAGAT

ATGAGAAGAACCTGGTGTTTGCCCAGAGATGGGGC

ATCAGAAAGGGCATTGTGATGGGATTCTTCACAGG

CTTTGTGTGGTGCCTGATCTTCCTGTGCTATGCCC

TGGCCTTTTGGTATGGCAGCACCCTGGTTCTTGAT

GAAGGGGAGTACACCCCTGGAACTCTGGTGCAGAT

CTTTCTGTCTGTGATTGTGGGAGCCCTGAACCTGG

GCAATGCCTCTCCATGTCTGGAAGCCTTTGCCACA

GGCAGAGCTGCTGCTACCAGCATCTTTGAGACAAT

TGACAGAAAGCCCATCATTGACTGCATGTCTGAGG

ATGGCTACAAGCTGGACAGGATCAAAGGGGAGATT

GAGTTCCACAACGTGACCTTTCACTACCCCAGCAG

ACCTGAAGTGAAGATCCTGAATGACCTGAACATGG

TCATCAAGCCTGGGGAGATGACAGCCCTTGTGGGA

CCTAGTGGTGCTGGCAAATCTACAGCCCTGCAGCT

GATCCAGAGATTCTATGACCCCTGTGAAGGCATGG

TCACAGTGGATGGCCATGACATCAGATCTCTGAAC

ATCCAGTGGCTGAGGGACCAGATTGGAATTGTGGA

ACAAGAGCCTGTGCTGTTCAGCACCACCATTGCAG

AGAACATCAGATATGGCAGGGAAGATGCCACAATG

GAAGATATTGTGCAGGCTGCCAAAGAGGCCAACGC

CTACAACTTCATCATGGACCTGCCTCAGCAGTTTG

ACACCCTTGTTGGAGAGGGTGGTGGCCAAATGAGT

GGTGGACAGAAACAGAGAGTGGCCATTGCTAGAGC

CCTGATCAGAAACCCCAAGATCCTGCTGCTGGACA

TGGCTACATCTGCCCCTGGACAATGAGTCTGAGGCT

ATGGTGCAAGAGGTGCTGAGCAAGATCCAGCATGG

CCACACCATCATTAGTGTGGCCCACAGACTGAGCA

CAGTCAGGGCTGCTGACACAATCATTGGATTTGAG

CATGGCACAGCAGTGGAAAGGGGCACCCATGAGGA

ACTGCTGGAAAGAAAAGGGGTCTACTTCACCCTGG

-continued

TCACCCTGCAGTCTCAGGGCAATCAGGCCCTGAAT
GAAGAGGACATCAAGGATGCCACTGAGGATGACAT
GCTGGCCAGAACCTTCAGCAGAGGCAGCTACCAGG
ATAGCCTGAGAGCCAGCATCAGACAGAGAAGCAAG
AGCCAGCTGAGCTACCTGGTGCATGAACCTCCACT
GGCTGTGGTGGACCACAAGTCCACCTATGAGGAAG
ATAGGAAGGACAAGGACATCCCTGTGCAAGAAGAG
GTGGAACCTGCTCCTGTCAGAAGAATCCTGAAGTT
TTCTGCCCCTGAGTGGCCCTACATGCTTGTGGGTT
CTGTTGGGGCTGCTGTGAATGGCACAGTGACCCCT
CTGTATGCCTTTCTGTTCTCCCAGATCCTGGGCAC
CTTTAGCATCCCTGACAAAGAGGAACAGAGGTCCC
AGATCAATGGTGTCTGCCTGCTCTTTGTGGCTATG
GGCTGTGTGTCCCTGTTTACCCAGTTCCTGCAGGG
ATATGCCTTTGCTAAGAGTGGGGAGCTGCTCACAA
AGAGGCTGAGAAAGTTTGGCTTCAGAGCCATGCTT
GGCCAGGACATTGCTTGGTTTGATGACCTGAGAAA
CAGCCCTGGGGCTCTGACCACAAGACTGGCTACAG
ATGCTAGCCAGGTGCAGGGTGCAGCAGGCAGCCAA
ATTGGCATGATTGTGAACAGCTTCACCAATGTGAC
AGTGGCCATGATCATTGCCTTCAGCTTCAGCTGGA
AACTGAGCCTTGTGATCCTCTGCTTCTTCCCCTTT
CTGGCCCTGTCTGGGGCTACCCAGACAAGAATGCT
GACTGGCTTTGCCTCCAGAGACAAGCAGGCCCTGG
AAATGGTTGGACAGATCACCAATGAGGCCCTGTCC
AACATCAGGACAGTGGCAGGCATTGGCAAAGAGAG
AAGATTCATTGAGGCCCTTGAGACAGAGCTTGAGA
AGCCCTTCAAGACAGCCATCCAGAAAGCTAACATC
TATGGGTTCTGCTTTGCTTTTGCCCAGTGCATCAT
GTTCATTGCCAACTCAGCCAGCTACAGATATGGTG
GCTACCTGATCTCTAATGAGGGCCTGCACTTCAGC
TATGTGTTCAGAGTGATCTCTGCTGTGGTGCTGTC
TGCCACTGCTCTGGGCAGAGCCTTTAGCTACACCC
CTAGCTATGCCAAAGCCAAGATCTCTGCAGCCAGA
TTCTTTCAGCTGCTGGATAGACAGCCTCCTATCAG
TGTGTACAACACAGCTGGGGAGAAGTGGGACAACT
TCCAGGGCAAGATTGACTTTGTGGATTGCAAGTTC
ACCTATCCTAGCAGACCAGACTCTCAGGTGCTGAA
TGGACTGAGTGTGTCTATCAGCCCTGGCCAGACAC
TGGCCTTTGTGGGAAGCTCTGGATGTGGCAAGAGC
ACCAGCATCCAGCTGCTTGAGAGGTTCTATGATCC

-continued

AGACCAGGGCAAAGTGATGATTGATGGGCATGACA
GCAAGAAAGTGAATGTGCAGTTCCTGAGGTCCAAC
ATTGGGATTGTGTCCCAAGAACCTGTTCTGTTTGC
CTGCAGCATCATGGATAACATTAAGTATGGGGACA
ACACCAAAGAAATCCCTATGGAAAGAGTGATTGCT
GCAGCCAAGCAGGCACAGCTGCATGATTTTGTGAT
GAGCCTGCCTGAGAAGTATGAGACAAATGTGGGCT
CCCAGGGCAGCCAGCTGTCTAGAGGGGAAAAACAG
AGAATTGCCATAGCCAGGGCCATAGTCAGAGATCC
TAAGATTCTGCTCCTGGATGAGGCCACCTCTGCTC
TGGATACAGAGTCTGAAAAGACAGTCCAGGTGGCA
CTGGACAAGGCCAGAGAGGGCAGAACCTGTATTGT
GATTGCCCATAGGCTGTCCACAATCCAAAATGCTG
ACATCATTGCAGTGATGGCCCAAGGGGTTGTGATT
GAGAAGGGAACACATGAAGAACTCATGGCCCAAAA
AGGGGCCTATTATAAGCTGGTCACCACTGGCAGCC
CCATCAGCTAG

Recombinant AAV vector comprising codon-optimized sequence encoding BSEP (rAAV-co-hBSEP)

(SEQ ID NO: 3)

CCTGCAGGCAGCTGCGCGCTCGCTCGCTCACTGAG
GCCGCCCGGGCAAAGCCCGGGCGTCGGGCGACCTT
TGGTCGCCCGGCCTCAGTGAGCGAGCGAGCGCGCA
GAGAGGGAGTGGCCAACTCCATCACTAGGGGTTCC
TGCGGCCGCGAATTCCATGGTACCAGGCATCAAGA
CACGTGCGCCACCCCCTCCACCTTGGACACAGGAC
GCTGTGGTTTCTGAGCCAGGTACAATGACTCCTTT
CGGTAAGTGCAGTGGAAGCTGTACACTGCCCAGGC
AAAGCGTCCGGGCAGCGTAGGCGGGCGACTCAGAT
CCCAGCCAGTGGACTTAGCCCCTGTTTGCTCCTCC
GATAACTGGGGTGACCTTGGTTAATATTCACCAGC
AGCCTCCCCCGTTGCCCCTCTGGATCCACTGCTTA
AATACGGACGAGGACAGGGCCCTGTCTCCTCAGCT
TCAGGCACCACCACTGACCTGGGACAGTGAAGGCC
TGTCGACGGATCCGAGCTCGCCGCCACCATGAGCG
ACTCCGTGATTCTGAGATCAATCAAAAAATTCGGC
GAAGAAAATGACGGGTTCGAGAGCGATAAATCCTA
TAATAATGACAAGAAGTCTAGGCTGCAGGACGAGA
AGAAGGGCGATGGCGTGCGGGTGGGCTTCTTTCAG
CTGTTCCGGTTCAGCAGCAGCACCGACATCTGGCT
GATGTTTGTGGGCAGCCTGTGCGCCTTCCTGCACG

-continued

GCATCGCACAGCCAGGCGTGCTGCTGATCTTTGGC

ACCATGACAGACGTGTTCATCGACTACGATGTGGA

GCTGCAGGAGCTGCAGATCCCTGGCAAAGCCTGCG

TGAACAATACCATCGTGTGGACAAACAGCTCCCTG

AACCAGAATATGACCAACGGCACACGCTGTGGCCT

GCTGAATATCGAGTCTGAGATGATCAAGTTTGCCA

GCTACTATGCAGGAATCGCAGTGGCCGTGCTGATC

ACCGGCTACATCCAGATTTGCTTCTGGGTCATCGC

AGCAGCAAGGCAGATCCAGAAGATGAGAAAGTTCT

ATTTTCGGAGAATCATGCGGATGGAGATCGGCTGG

TTTGACTGTAACTCTGTGGGCGAGCTGAATACAAG

ATTCAGCGACGACATCAACAAGATCAATGACGCCA

TCGCCGATCAGATGGCCCTGTTTATCCAGCGGATG

ACCAGCACAATCTGTGGCTTCCTGCTGGGCTTCTT

TAGAGGCTGGAAGCTGACCCTGGTCATCATCAGCG

TGTCCCCACTGATCGGAATCGGAGCAGCAACAATC

GGCCTGTCTGTGAGCAAGTTCACCGACTACGAGCT

GAAAGCCTACGCCAAGGCAGGAGTGGTGGCAGATG

AAGTGATCAGCAGCATGAGGACCGTGGCAGCCTTT

GGCGGAGAGAAGAGGGAGGTGGAGCGGTACGAGAA

GAACCTGGTGTTCGCCCAGCGGTGGGGCATCAGAA

AGGGCATCGTGATGGGCTTCTTTACAGGCTTCGTG

TGGTGCCTGATCTTCCTGTGCTACGCCCTGGCCTT

TTGGTATGGCTCCACCCTGGTGCTGGACGAGGGAG

AGTATACCCCTGGCACACTGGTGCAGATTTTCCTG

AGCGTGATCGTGGGCGCCCTGAACCTGGGAAATGC

ATCCCCATGCCTGGAAGCCTTCGCCACAGGAAGGG

CAGCAGCCACCTCCATCTTCGAGACAATCGACCGC

AAGCCTATCATCGACTGTATGTCTGAGGATGGCTA

CAAGCTGGACAGGATCAAGGGCGAGATCGAGTTTC

ACAATGTGACCTTCCACTATCCCAGCCGCCCTGAG

GTGAAGATCCTGAACGATCTGAATATGGTCATCAA

GCCAGGAGAGATGACCGCCCTGGTGGGACCCTCTG

GAGCAGGCAAGAGCACCGCCCTGCAGCTGATCCAG

CGGTTTTACGACCCTTGCGAGGGAATGGTGACCGT

GGACGGACACGACATCAGGTCCCTGAACATCCAGT

GGCTGCGCGATCAGATCGGCATCGTGGAGCAGGAG

CCAGTGCTGTTCTCTACCACAATCGCCGAGAATAT

CAGATACGGCCGCGAGGATGCCACAATGGAGGACA

TCGTGCAGGCCGCCAAGGAGGCCAACGCCTATAAC

TTCATCATGGATCTGCCCCAGCAGTTCGACACCCT

GGTGGGAGAGGGAGGAGGACAGATGTCCGGAGGCC

AGAAGCAGAGAGTGGCCATCGCCAGAGCCCTGATC

CGCAACCCTAAGATCCTGCTGCTGGATATGGCCAC

AAGCGCCCTGGACAATGAGTCCGAGGCTATGGTGC

AGGAGGTGCTGAGCAAGATCCAGCACGGCCACACC

ATCATCTCTGTGGCACACAGGCTGAGCACAGTGAG

AGCAGCCGACACCATCATCGGCTTTGAGCACGGCA

CAGCAGTGGAGAGGGGCACCCACGAGGAGCTGCTG

GAGAGGAAGGGCGTGTACTTCACCCTGGTGACACT

GCAGTCCCAGGGCAACCAGGCCCTGAATGAGGAGG

ACATCAAGGATGCCACAGAGGACGATATGCTGGCC

CGGACCTTCAGCAGAGGCTCCTATCAGGATTCTCT

GAGGGCCAGCATCAGGCAGCGGAGCAAGTCTCAGC

TGAGCTACCTGGTGCACGAGCCACCTCTGGCAGTG

GTGGACCACAAGTCCACCTATGAGGAGGATCGCAA

GGACAAGGACATCCCAGTGCAGGAGGAGGTGGAGC

CTGCACCAGTGAGGCGCATCCTGAAGTTTTCCGCC

CCAGAGTGGCCCTACATGCTGGTGGGATCTGTGGG

AGCAGCAGTGAACGGCACCGTGACACCACTGTATG

CCTTCCTGTTTTCCCAGATCCTGGGCACCTTCTCT

ATCCCCGACAAGGAGGAGCAGCGGTCCCAGATCAA

TGGCGTGTGCCTGCTGTTTGTGGCTATGGGCTGCG

TGAGCCTGTTTACACAGTTCCTGCAGGGCTACGCC

TTCGCCAAGAGCGGCGAGCTGCTGACCAAGCGGCT

GAGAAAGTTCGGCTTTAGAGCCATGCTGGGCCAGG

ACATCGCCTGGTTTGACGATCTGCGGAACAGCCCA

GGCGCCCTGACCACAAGACTGGCCACAGATGCATC

TCAGGTGCAGGGAGCAGCAGGCAGCCAGATCGGCA

TGATCGTGAACTCCTTCACCAATGTGACAGTGGCC

ATGATCATCGCCTTCAGCTTTTCCTGGAAGCTGAG

CCTGGTCATCCTGTGCTTCTTCCCCTTTCTGGCCC

TGAGCGGAGCAACCCAGACAAGGATGCTGACCGGC

TTCGCCTCCAGAGACAAGCAGGCCCTGGAGATGGT

GGGCCAGATCACAAACGAGGCCCTGAGCAATATCA

GGACCGTGGCAGGAATCGGCAAGGAGCGGCGGTTC

ATCGAGGCCCTGGAGACAGAGCTGGAGAAGCCTTT

CAAGACCGCCATCCAGAAGGCCAACATCTACGGCT

TCTGCTTTGCCTTCGCCCAGTGTATCATGTTCATC

GCCAACTCTGCCAGCTACCGCTATGGCGGCTACCT

GATCAGCAATGAGGGCCTGCACTTCAGCTACGTGT

-continued

TCAGAGTGATCAGCGCCGTGGTGCTGTCTGCCACA

GCCCTGGGAAGGGCCTTCTCCTACACCCCATCTTA

TGCCAAGGCCAAGATCAGCGCCGCCAGGTTCTTTC

AGCTGCTGGACCGCCAGCCACCCATCAGCGTGTAC

AACACAGCCGGCGAGAAGTGGGATAATTTCCAGGG

CAAGATCGACTTTGTGGATTGCAAGTTCACCTATC

CTAGCAGACCAGACTCCCAGGTGCTGAATGGCCTG

TCCGTGTCTATCAGCCCAGGCCAGACACTGGCCTT

TGTGGGCTCCTCTGGCTGTGGCAAGTCCACCTCTA

TCCAGCTGCTGGAGCGGTTCTATGACCCCGATCAG

GGCAAAGTGATGATCGACGGCCACGATAGCAAGAA

GGTGAACGTGCAGTTTCTGAGATCCAATATCGGCA

TCGTGTCTCAGGAGCCTGTGCTGTTCGCCTGCTCC

ATCATGGATAACATCAAGTACGGCGACAATACAAA

GGAGATCCCAATGGAGAGAGTGATCGCAGCAGCAA

AGCAGGCACAGCTGCACGATTTCGTGATGTCCCTG

CCCGAGAAGTATGAGACAAACGTGGGCTCTCAGGG

CAGCCAGCTGTCCAGGGGCGAGAAGCAGAGGATCG

CAATCGCCAGGGCCATCGTGCGCGATCCCAAGATC

CTGCTGCTGGACGAGGCCACCAGCGCCCTGGATAC

AGAGTCCGAGAAGACCGTGCAGGTGGCCCTGGACA

AGGCCCGGGAGGGAAGAACATGTATCGTGATCGCC

CACAGACTGAGCACCATCCAGAATGCCGACATCAT

CGCCGTGATGGCCCAGGGCGTGGTCATCGAGAAGG

GCACCCACGAGGAACTGATGGCACAGAAAGGGGCT

TACTACAAACTGGTCACAACAGGCTCACCTATCTC

ATAGGGATCCATATGATATCAATAAAGACCTCTTA

TTTTCATTCATCAGGTGTGGTTGGTTTTTTTGTGT

GGGGGCTCGAGATCTGAGGAACCCCTAGTGATGGA

GGCGGCCGCAGGAACCCCTAGTGATGGAGTTGGCC

ACTCCCTCTCTGCGCGCTCGCTCGCTCACTGAGGC

CGGGCGACCAAAGGTCGCCCGACGCCCGGGCTTTG

CCCGGGCGGCCTCAGTGAGCGAGCGAGCGCGCAGC

TGCCTGCAG

Recombinant AAV vector comprising codon-optimized sequence encoding BSEP #2 (rAAV-co-hBSEP-2)

(SEQ ID NO: 4)

CCTGCAGGCAGCTGCGCGCTCGCTCGCTCACTGAG

GCCGCCCGGGCAAAGCCCGGGCGTCGGGCGACCTT

TGGTCGCCCGGCCTCAGTGAGCGAGCGAGCGCGCA

GAGAGGGAGTGGCCAACTCCATCACTAGGGGTTCC

TGCGGCCGCGAATTCCATGGTACCAGGCATCAAGA

-continued

CACGTGCGCCACCCCCTCCACCTTGGACACAGGAC

GCTGTGGTTTCTGAGCCAGGTACAATGACTCCTTT

CGGTAAGTGCAGTGGAAGCTGTACACTGCCCAGGC

AAAGCGTCCGGGCAGCGTAGGCGGGCGACTCAGAT

CCCAGCCAGTGGACTTAGCCCCTGTTTGCTCCTCC

GATAACTGGGGTGACCTTGGTTAATATTCACCAGC

AGCCTCCCCCGTTGCCCCTCTGGATCCACTGCTTA

AATACGGACGAGGACAGGGCCCTGTCTCCTCAGCT

TCAGGCACCACCACTGACCTGGGACAGTGAAGGCC

TGTCGACGGATCCGAGCTCGCCGCCACCATGTCTG

ATTCTGTGATCCTGAGATCCATCAAGAAATTTGGG

GAAGAGAATGATGGCTTTGAGTCTGACAAGAGCTA

CAACAATGACAAGAAAAGCAGGCTGCAGGATGAGA

AAAAGGGTGATGGTGTCAGAGTGGGCTTCTTCCAG

CTGTTCAGATTCAGCAGCAGCACAGACATCTGGCT

GATGTTTGTGGGCAGCCTGTGTGCCTTCCTGCATG

GAATTGCTCAGCCTGGGGTGCTGCTGATCTTTGGC

ACCATGACAGATGTGTTCATTGACTATGATGTGGA

ACTGCAAGAGCTGCAGATCCCTGGCAAGGCTTGTG

TGAACAACACCATTGTGTGGACCAACAGCAGCCTG

AACCAGAACATGACCAATGGCACCAGATGTGGCCT

GCTGAACATAGAGTCTGAGATGATCAAGTTTGCCA

GCTACTATGCTGGCATTGCTGTGGCAGTGCTGATC

ACAGGCTACATCCAGATCTGCTTTTGGGTCATAGC

TGCTGCCAGACAGATCCAGAAGATGAGGAAGTTCT

ACTTTAGAAGGATCATGAGGATGGAAATTGGATGG

TTTGACTGCAACTCTGTGGGAGAGCTGAACACCAG

ATTCTCTGATGACATCAACAAGATCAATGATGCCA

TTGCTGACCAGATGGCCCTGTTCATCCAGAGGATG

ACCAGCACCATCTGTGGCTTTCTGCTGGGCTTTTT

CAGAGGCTGGAAGCTGACCCTGGTTATCATCTCTG

TGTCCCCACTGATTGGCATTGGAGCTGCCACCATT

GGCCTGTCTGTGTCCAAGTTCACAGACTATGAGCT

GAAAGCCTATGCCAAGGCTGGTGTTGTGGCTGATG

AAGTGATCAGCTCCATGAGAACAGTGGCTGCCTTT

GGTGGTGAAAAGAGGGAAGTTGAGAGATATGAGAA

GAACCTGGTGTTTGCCCAGAGATGGGGCATCAGAA

AGGGCATTGTGATGGGATTCTTCACAGGCTTTGTG

TGGTGCCTGATCTTCCTGTGCTATGCCCTGGCCTT

TTGGTATGGCAGCACCCTGGTTCTTGATGAAGGGG

-continued

AGTACACCCCTGGAACTCTGGTGCAGATCTTTCTG
TCTGTGATTGTGGGAGCCCTGAACCTGGGCAATGC
CTCTCCATGTCTGGAAGCCTTTGCCACAGGCAGAG
CTGCTGCTACCAGCATCTTTGAGACAATTGACAGA
AAGCCCATCATTGACTGCATGTCTGAGGATGGCTA
CAAGCTGGACAGGATCAAAGGGGAGATTGAGTTCC
ACAACGTGACCTTTCACTACCCCAGCAGACCTGAA
GTGAAGATCCTGAATGACCTGAACATGGTCATCAA
GCCTGGGGAGATGACAGCCCTTGTGGGACCTAGTG
GTGCTGGCAAATCTACAGCCCTGCAGCTGATCCAG
AGATTCTATGACCCCTGTGAAGGCATGGTCACAGT
GGATGGCCATGACATCAGATCTCTGAACATCCAGT
GGCTGAGGGACCAGATTGGAATTGTGGAACAAGAG
CCTGTGCTGTTCAGCACCACCATTGCAGAGAACAT
CAGATATGGCAGGGAAGATGCCACAATGGAAGATA
TTGTGCAGGCTGCCAAAGAGGCCAACGCCTACAAC
TTCATCATGGACCTGCCTCAGCAGTTTGACACCCT
TGTTGGAGAGGGTGGTGGCCAAATGAGTGGTGGAC
AGAAACAGAGAGTGGCCATTGCTAGAGCCCTGATC
AGAAACCCCAAGATCCTGCTGCTGGACATGGCTAC
ATCTGCCCTGGACAATGAGTCTGAGGCTATGGTGC
AAGAGGTGCTGAGCAAGATCCAGCATGGCCACACC
ATCATTAGTGTGGCCCACAGACTGAGCACAGTCAG
GGCTGCTGACACAATCATTGGATTTGAGCATGGCA
CAGCAGTGGAAAGGGGCACCCATGAGGAACTGCTG
GAAAGAAAAGGGGTCTACTTCACCCTGGTCACCCT
GCAGTCTCAGGGCAATCAGGCCCTGAATGAAGAGG
ACATCAAGGATGCCACTGAGGATGACATGCTGGCC
AGAACCTTCAGCAGAGGCAGCTACCAGGATAGCCT
GAGAGCCAGCATCAGACAGAGAAGCAAGAGCCAGC
TGAGCTACCTGGTGCATGAACCTCCACTGGCTGTG
GTGGACCACAAGTCCACCTATGAGGAAGATAGGAA
GGACAAGGACATCCCTGTGCAAGAAGAGGTGGAAC
CTGCTCCTGTCAGAAGAATCCTGAAGTTTTCTGCC
CCTGAGTGGCCCTACATGCTTGTGGGTTCTGTTGG
GGCTGCTGTGAATGGCACAGTGACCCCTCTGTATG
CCTTTCTGTTCTCCCAGATCCTGGGCACCTTTAGC
ATCCCTGACAAAGAGGAACAGAGGTCCCAGATCAA
TGGTGTCTGCCTGCTCTTTGTGGCTATGGGCTGTG
TGTCCCTGTTTACCCAGTTCCTGCAGGGATATGCC
TTTGCTAAGAGTGGGGAGCTGCTCACAAAGAGGCT

-continued

GAGAAAGTTTGGCTTCAGAGCCATGCTTGGCCAGG
ACATTGCTTGGTTTGATGACCTGAGAAACAGCCCT
GGGGCTCTGACCACAAGACTGGCTACAGATGCTAG
CCAGGTGCAGGGTGCAGCAGGCAGCCAAATTGGCA
TGATTGTGAACAGCTTCACCAATGTGACAGTGGCC
ATGATCATTGCCTTCAGCTTCAGCTGGAAACTGAG
CCTTGTGATCCTCTGCTTCTTCCCCTTTCTGGCCC
TGTCTGGGGCTACCCAGACAAGAATGCTGACTGGC
TTTGCCTCCAGAGACAAGCAGGCCCTGGAAATGGT
TGGACAGATCACCAATGAGGCCCTGTCCAACATCA
GGACAGTGGCAGGCATTGGCAAAGAGAGAAGATTC
ATTGAGGCCCTTGAGACAGAGCTTGAGAAGCCCTT
CAAGACAGCCATCCAGAAAGCTAACATCTATGGGT
TCTGCTTTGCTTTTGCCCAGTGCATCATGTTCATT
GCCAACTCAGCCAGCTACAGATATGGTGGCTACCT
GATCTCTAATGAGGGCCTGCACTTCAGCTATGTGT
TCAGAGTGATCTCTGCTGTGGTGCTGTCTGCCACT
GCTCTGGGCAGAGCCTTTAGCTACACCCCTAGCTA
TGCCAAAGCCAAGATCTCTGCAGCCAGATTCTTTC
AGCTGCTGGATAGACAGCCTCCTATCAGTGTGTAC
AACACAGCTGGGGAGAAGTGGGACAACTTCCAGGG
CAAGATTGACTTTGTGGATTGCAAGTTCACCTATC
CTAGCAGACCAGACTCTCAGGTGCTGAATGGACTG
AGTGTGTCTATCAGCCCTGGCCAGACACTGGCCTT
TGTGGGAAGCTCTGGATGTGGCAAGAGCACCAGCA
TCCAGCTGCTTGAGAGGTTCTATGATCCAGACCAG
GGCAAAGTGATGATTGATGGGCATGACAGCAAGAA
AGTGAATGTGCAGTTCCTGAGGTCCAACATTGGGA
TTGTGTCCCAAGAACCTGTTCTGTTTGCCTGCAGC
ATCATGGATAACATTAAGTATGGGGACAACACCAA
AGAAATCCCTATGGAAAGAGTGATTGCTGCAGCCA
AGCAGGCACAGCTGCATGATTTTGTGATGAGCCTG
CCTGAGAAGTATGAGACAAATGTGGGCTCCCAGGG
CAGCCAGCTGTCTAGAGGGGAAAAACAGAGAATTG
CCATAGCCAGGGCCATAGTCAGAGATCCTAAGATT
CTGCTCCTGGATGAGGCCACCTCTGCTCTGGATAC
AGAGTCTGAAAAGACAGTCCAGGTGGCACTGGACA
AGGCCAGAGAGGGCAGAACCTGTATTGTGATTGCC
CATAGGCTGTCCACAATCCAAAATGCTGACATCAT
TGCAGTGATGGCCCAAGGGGTTGTGATTGAGAAGG

-continued

GAACACATGAAGAACTCATGGCCCAAAAAGGGGCC

TATTATAAGCTGGTCACCACTGGCAGCCCCATCAG

CTAGGGATCCATATGATATCAATAAAGACCTCTTA

TTTTCATTCATCAGGTGTGGTTGGTTTTTTTGTGT

GGGGGCTCGAGATCTGAGGAACCCCTAGTGATGGA

GGCGGCCGCAGGAACCCCTAGTGATGGAGTTGGCC

ACTCCCTCTCTGCGCGCTCGCTCGCTCACTGAGGC

CGGGCGACCAAAGGTCGCCCGACGCCCGGGCTTTG

CCCGGGCGGCCTCAGTGAGCGAGCGAGCGCGCAGC

TGCCTGCAG

Alpha 1 antitrypsin promoter
(SEQ ID NO: 5)

CGCCACCCCCTCCACCTTGGACACAGGACGCTGTG

GTTTCTGAGCCAGGTACAATGACTCCTTTCGGTAA

GTGCAGTGGAAGCTGTACACTGCCCAGGCAAAGCG

TCCGGGCAGCGTAGGCGGGCGACTCAGATCCCAGC

CAGTGGACTTAGCCCCTGTTTGCTCCTCCGATAAC

-continued

TGGGGTGACCTTGGTTAATATTCACCAGCAGCCTC

CCCCGTTGCCCCTCTGGATCCACTGCTTAAATACG

GACGAGGACA

Human minimal bile salt export pump (ABCB11) gene promoter
(SEQ ID NO: 6)

TTCCCAAGCACACTCTGTGTTTGGGGTTATTGCTC

TGAGTATGTTTCTCGTATGTCACTGAACTGTGCTT

GGGCTGCCCTTAGGGACATTGATCCTTAGGCAAAT

AGATAATGTTCTTGAAAAAGTTTGAATTCTGTTCA

GTGCT

Mouse minimal Bile Salt export pump (ABCB11) gene promoter
(SEQ ID NO: 7)

GGTTCCTGCTTTGAGTATGTTCGACCTTTCCTCTC

ATGTCACTGAACTGTGCTAGATCTGGACTTTAGGC

CATTGACCTATAAGCAAATAGATAGTGTTCTTAAA

AAAGCCTGATTTCTGTTCAATGCTTTATTACCATG

AAAAC

Synthetic poly A sequence
(SEQ ID NO: 8)

AATAAAGACCTCTTATTTTCATTCATCAGGTGTGG

TTGGTTTTTTTGTGTGGGGGC

---

The invention claimed is:

1. A nucleic acid construct comprising a nucleic acid sequence encoding BSEP having SEQ ID NO: 1 or SEQ ID NO: 2.

2. The nucleic acid construct of claim 1 further comprising a liver-specific promoter.

3. The nucleic acid construct of claim 1 further comprising a polyadenylation signal sequence.

4. The nucleic acid construct of claim 1 further comprising 5'ITR and 3'ITR sequences of AAV.

5. The nucleic acid construct of claim 1 comprising a nucleic acid sequence of SEQ ID NO: 3 or SEQ ID NO: 4.

6. An expression vector comprising the nucleic acid construct of claim 1.

7. The expression vector of claim 6 wherein said vector is a viral vector.

8. A viral particle comprising the nucleic acid construct of claim 1.

9. An AAV particle comprising the nucleic acid construct of claim 1.

10. A host cell comprising the nucleic acid construct of claim 1.

11. A pharmaceutical composition comprising the nucleic acid construct of claim 1, and a pharmaceutically acceptable excipient.

12. A method of treating Progressive Familial Intrahepatic Cholestasis Type 2 (PFIC2) in a subject in need thereof comprising administering to the subject a therapeutically effective amount of the nucleic acid construct of claim 1.

13. The method of claim 12 wherein said subject is a neonate, an infant, a child or an adult.

14. A method of producing the viral particle of claim 8, comprising:

a) culturing a packaging cell comprising the nucleic acid construct in a culture medium, and b) harvesting the viral particle from cell culture supernatant and/or inside the packaging cell.

15. A kit comprising the nucleic acid construct of claim 1, in one or more containers.

16. The nucleic acid construct of claim 1 comprising SEQ ID NO: 1.

17. The nucleic acid construct of claim 1 comprising SEQ ID NO: 2.

18. The nucleic acid construct of claim 2 wherein the liver-specific promoter is an alpha-1-antitrypsin promoter or a bile salt-inducible promoter.

19. The nucleic acid construct of claim 3 wherein the polyadenylation signal sequence comprises SEQ ID NO: 8.

* * * * *